US006958324B2

(12) United States Patent
Salzman et al.

(10) Patent No.: US 6,958,324 B2
(45) Date of Patent: Oct. 25, 2005

(54) INOSINE COMPOUNDS AND THEIR USE FOR TREATING OR PREVENTING AN INFLAMATION OR A REPERFUSION DISEASE

(75) Inventors: Andrew L. Salzman, Belmont, MA (US); Csaba Szabo, Gloucester, MA (US)

(73) Assignee: Inotek Pharmaceuticals Corporation, Beverly, MA (US)

( * ) Notice: Subject to any disclaimer, the term of this patent is extended or adjusted under 35 U.S.C. 154(b) by 0 days.

(21) Appl. No.: 10/107,080

(22) Filed: Mar. 26, 2002

(65) Prior Publication Data

US 2003/0040502 A1 Feb. 27, 2003

Related U.S. Application Data

(60) Continuation-in-part of application No. 09/817,829, filed on Mar. 26, 2001, now abandoned, and a continuation-in-part of application No. 09/986,206, filed on Oct. 19, 2001, now abandoned, which is a continuation-in-part of application No. 09/626,602, filed on Jul. 27, 2000, now abandoned, which is a continuation-in-part of application No. 09/491,888, filed on Jan. 24, 2000, now abandoned, which is a continuation-in-part of application No. 09/452,427, filed on Dec. 1, 1999, now abandoned, which is a division of application No. 09/626,602, filed on Jul. 27, 2000, now abandoned.

(60) Provisional application No. 60/110,562, filed on Dec. 2, 1998.

(51) Int. Cl.$^7$ ......................... A61K 31/70; A61K 31/52; A61K 31/335
(52) U.S. Cl. ........................... 514/45; 514/48; 514/262; 514/266; 514/449
(58) Field of Search ................................. 514/247, 261, 514/262, 266, 449, 45, 48

(56) References Cited

U.S. PATENT DOCUMENTS

| | | |
|---|---|---|
| 3,407,190 A | 10/1968 | Honjo et al. |
| 4,459,292 A | 7/1984 | Andermann et al. |
| 4,870,002 A | 9/1989 | Kiel |
| 5,234,922 A | 8/1993 | Welsh et al. |
| 5,260,275 A | 11/1993 | Cooper et al. |
| 5,614,504 A | 3/1997 | Hadden et al. |
| 5,856,360 A | 1/1999 | Salzman et al. |
| 5,922,769 A | 7/1999 | Barelli et al. |
| 6,060,459 A | 5/2000 | von Borstel et al. |
| 6,150,383 A | 11/2000 | Ikeda et al. |
| 6,342,484 B1 | 1/2002 | Kulkarni et al. |

FOREIGN PATENT DOCUMENTS

| | | |
|---|---|---|
| EP | 0688766 | 12/1995 |
| EP | 0749751 | 12/1996 |
| EP | 1153931 | 11/2001 |
| JP | 53-044471 | 11/1978 |
| NL | 6610578 | 1/1967 |
| RU | 214899 | 5/2000 |
| RU | 215336 | 7/2000 |
| RU | 2160591 | 12/2000 |
| WO | WO 90/09792 | 9/1990 |
| WO | WO 96/09823 | 4/1996 |
| WO | WO 96/33203 | 10/1996 |
| WO | WO 97/17975 | 5/1997 |
| WO | WO 98/56378 | 12/1998 |
| WO | WO 99/18932 | 4/1999 |
| WO | WO 99/37151 | 7/1999 |
| WO | WO 00/47601 | 8/2000 |

OTHER PUBLICATIONS

Almawi et al., 1999, "Clinical review 103: T helper type 1 and 2 cytokines mediate the onset and progression of type I (insulin–dependent) diabetes", J. Clin. Endocrinol. Metab. 84:1497–1502.

Bankers–Fulbright et al., 1998, "Sulfonylureas inhibit cytokine–induced eosinophil survival and activation", J. Immunol. 160–5546–5553.

Dielman et al., 1997, "Role of animal models for the pathogenesis and treatment of inflammatory bowel disease"; Scand. J. Gastroenterol. Suppl. 223:99–104.

Dunning, 1999, "Nateglinide; a glucose–sensitive insulinotropic agent that is chemically and pharmacologically distinct from the sulfonylureas", Curr. Opin. Endocrinol. Diabetes 6(suppl. 1):S29–S31.

Gaudio et al., 1999, "Dextran sulfate sodium (DSS) colitis in rats: clinical, structural, and ultrastructural aspects", Dig. Dis. Sci. 44:1458–1475.

Green, 1981, *Protective Groups in Organic Synthesis*, John Wiley & Sons, (table of contents).

Hasko et al., 2000, "Inosine inhibits inflammatory cytokine production by a posttranscriptional mechanism and protects against endotoxin–induced shock", J. Immunol. 164:1013–1019.

Hasko et al., 1999, "Inosine inhibits inflammatory cytokine production by a posttranscriptional mechanism and protects against endotoxin–induced shock", J. Am. Soc. Hematol. 94:427a (abstract No. 1893).

Jurkowitz et al., 1998, "Adenosine, inosine and guanosine protect glial cells during glucose deprivation and mitochondrial inhibition: correlation between protection and ATP preservation", J. Neurochem. 71:535–548.

Kimura et al., "Determination of the active molety of BX661A, a new therapeutic agent for ulcerative colitis, by studying its therapeutic effects on ulcerative colitis induced by dextran sulfate sodium in rats", Arzneimittelforschung 48:1091–1096.

(Continued)

Primary Examiner—Shengjun Wang
Assistant Examiner—Jennifer Kim
(74) Attorney, Agent, or Firm—Wilmer Cutler Pickerinf Hale and Dorr LLP

(57) ABSTRACT

Inosine compounds, compositions comprising an inosine compound and methods for treating or preventing an inflammation disease or a reperfusion disease comprising administering an effective amount of an inosine compound to a patient in need thereof are disclosed.

29 Claims, 8 Drawing Sheets

OTHER PUBLICATIONS

Kipshidze et al., 1983, "Inosine effect on high-energy phosphate content, mechanical activity of glycerinated fiber bundles, morphology and microcirculation in myocardium in toxi-allergic myocarditis", Methods Find. Exp. Clin. Pharmacol. 5:163–170.

Kolb et al., 1987, "Analysis of 22 immunomodulatory substances for efficacy in low-dose streptozotocin-induced diabetes", Diabetes Res. 6:21–27.

Kuninaka et al., 1980, "Flavor activity of sulfur-containing compounds related to flavor nucleotides", Agric. Biol. Chem. 44:1437–1439.

March, 1992, in: *Advanced Organic Chemistry, Reaction Mechanisms and Structure* $4^{th}$ ed., John Wiley& Sons, pp. 404–408.

Murthy et al., 1999, "Combination therapy of pentoxifylline and TNFα monoclonal antibody in dextran sulphate-induced mouse colitis", Ailment Pharmacol Ther.13:251–260.

Norton et al., 2001, "Use of nucleotides in weanling rats with diarrhea induced by a lactose overload: effect on the evolution of diarrhea and weight and on the histopathology of intestine, liver and spleen", Braz. J. Med. Biol. Res. 34:195–202.

Perfetti et al., 1998, "Novel therapeutic strategies for the treatment of type 2 diabetes", Diabetes Metab. Rev. 14:207–225.

Qiu et al., 2000, "IMP and AMP deaminase in reperfusion injury down-regulates neutrophil recruitment", Proc. Natl. Acad. Sci. USA 97:4267–4272.

Rabinovitch et al., 1998, "Cytokines and their roles in pancreatic islet beta-cell destruction and insulin-dependent diabetes mellitus", Biochem. Pharmacol. 55:1139–1149.

Sasaki et al., 2000, "Prostaglandin E2 inhibits lesion formation in dextran sodium sulphate-induced colitis in rats and reduces the levels of mucosal inflammatory cytokines", Scand. J. Immunol. 51:23–28.

Szabo et al., 1998, "Supression of macrophage inflammatory protein (MIP)-1alpha production and collagen-induced arthritis by adenosine receptor agonists", Brit. J. Pharm. 125–397–398.

Veerabagu et al., 1996, "Intravenous nucleosides and a nucleotide promote healing of small bowel ulcers in experimental enterocolitis", Dig. Dis. Sci. 41:1452–1457.

Wada et al., 2001, "Inosine monophoshate and aspirin-triggered 15-epi-lipoxin A4 act in concert to regulate neutrophil trafficking: additive actions of two new endogenous anti-inflammatory mediators", J. Hematother. Stem Cell Res, 10:75–79.

FIG. 1 A-E

INOSINE COMPOUNDS AND THEIR USE FOR TREATING OR PREVENTING AN INFLAMATION OR A REPERFUSION DISEASE

This application is (a) a continuation-in-part of U.S. application Ser. No. 09/817,829, filed Mar. 26, 2001 now abandoned, which is a continuation-in-part of U.S. application Ser. No. 09/626,602, filed Jul. 27, 2000 now abandoned, which is a continuation-in-part of U.S. application Ser. No. 09/491,888, filed Jan. 24, 2000 now abandoned, which is a continuation-in-part of U.S. application Ser. No. 09/452,427, filed Dec. 1, 1999 now abandoned, which claims the benefit of U.S. Provisional Application No. 60/110,562, filed Dec. 2, 1998; and (b) a continuation-in-part of U.S. application Ser. No. 09/986,206, filed Oct. 19, 2001 abandoned, which is a division of U.S. application Ser. No. 09/626,602, filed Jul. 27, 2000 abandoned, the entire disclosure of each of the aforementioned applications being incorporated by reference herein in its entirety.

1. FIELD OF THE INVENTION

The invention relates to inosine compounds, compositions comprising an inosine compound and methods for treating or preventing an inflammation disease or a reperfusion disease.

2. BACKGROUND OF THE INVENTION

Various forms of inflammation are characterized by activation of macrophages. Macrophages are thought to induce and maintain inflammatory processes mainly by producing various products that, by acting on other cells, bring about the deleterious consequences of inflammation. For example, macrophages produce cytokines. These proteins are central mediators in inflammatory processes, such as the local inflammatory processes characteristic of arthritis or colitis. Cytokines produced by macrophages are also thought to be involved in systemic inflammatory processes, such as endotoxic shock. Macrophage products are more generally involved in pathophysiological mechanisms, such as plasma extravasation, inflammatory cell diapedesis, release of toxic free radicals, endothelial injury, and release of tissue degrading enzymes, which can result in tissue injury and, ultimately, organ failure.

Tumor necrosis factor (TNF) is a cytokine associated with macrophage activation. TNF is also thought to be involved in inducing most of the pathophysiological events characteristic of inflammation. For example, TNF is a key cytokine in associated with the toxic effect of endotoxin (LPS) and in the pathogenesis of septic shock, as evidenced by high serum plasma levels of TNF after LPS administration to animals or to human volunteers, or in septic subjects. Administration of anti-TNF antibodies protects against the lethal effects of LPS and of live bacteria in a variety of animal models. Moreover, TNF can be a central target in the treatment of rheumatoid arthritis.

Interleukin-12 (IL-12) is another macrophage product that has been shown to be involved in the induction of pathology in several inflammatory diseases. These diseases include autoimmune diseases such as multiple sclerosis, inflammatory bowel disease, insulin dependent diabetes mellitus, and rheumatoid arthritis, and inflammatory states such as septic shock and the generalized Schwarzman reaction. For example, administration of anti-IL-12 antibodies substantially reduces the incidence and severity of adoptively transferred experimental allergic encephalomyclitis, suggesting that endogenous IL-12 is involved in its pathogenesis. Furthermore, the course of disease in adjuvant-induced arthritis is suppressed in IL-12 deficient mice, or in mice treated with anti-mIL-12 antibodies.

The chemokine macrophage inflammatory protein (MIP)-1a and the CXC chemokine MIP-2 are additional proinflammatory proteins expressed by macrophages.

IDDM (insulin-dependent diabetes mellitus), Type 1 diabetes, is a consequence of the destruction of pancreatic β-cells. Rabinovitch, A. and Wilma L. Suarez-Pinzon, *Cytokines and Their Roles in Pancreatic Islet β-Cell Destruction and Insulin-Dependent Diabetes Mellitus*, Biochemical Pharmacology, Vol. 55, 1998, pp. 1139–1149. The Type 1 cytokines, produced by Th1 cells, cause destruction of pancreatic β-cells. Type 2 cytokines, produced by Th2 cells, suppress the activity of the Type 1 cytokines. Almawi, et al., *T Helper Type 1 and 2 Cytokines Mediate the Onset and Progression of Type I (Insulin-Dependent) Diabetes*, JCE & M, Vol. 84, No. 5, 1999, pp. 1497–1502 discloses that both Th1 and Th2 cells affect the onset and the progression of type I diabetes.

U.S. Pat. No. 6,342,484 to Kulkami et al. discloses that inosine promotes healing in a diabetic patient.

Kuninaka et al, *Flavor Activity of Sulfur-containing Compounds Related to Flavor Nucleotides*, Agric. Biol. Chem, 44 (6), 1980, pp. 1437–1439 discloses that inosine-5'-monophosphate, inosine-5'-monosulfate, inosine-2',(3'), 5'-diphosphate and inosine-2',(3'), 5'-disulfate affect taste sensation.

U.S. Pat. No. 5,614,504 to Hadden et al. discloses a method of preparing methyl 5'-inosine monophosphate (MIMP) and its use for reversing inflammation and physical trauma.

Jurkowitz et al., *Adenosine, Inosine, and Guanosine Protect Gilian Cells During Glucose Deprivation and Mitochondrial Inhibition: Correlation Between Protection and STP Preservation*, J. Neurochem., Vol. 71, No. 2, 1998, pp. 535–548 discloses that inosine can delay cell death by retarding the decline of ATP.

G. Hasko et al., Abstracts, Blood, Vol. 94, No. 10, 1999, p. 427a, Abstract No. 1893 discloses that inosine can suppress proinflammatory cytokine production and reduce mortality in a mouse endotoxemic model.

Haskó et al., *Inosine Inhibits Inflammatory Cytokine Production by a Posttranscriptional Mechanism and Protects Against Endotoxin-Induced Shock*, J. Immunol., 2000, pp. 1013–1019 discloses using inosine to inhibit the production of proinflammatory cytokines.

K. Wada et al., *Inosine Monophoshpate and Aspirin-Triggered 15-Epilipoxin A4 Act in Concert to Regulate Neutrophil Trafficking: Additive Actions of Two New Endogeneous Anti-Inflammatory Mediators*, J. Hematother. Stem Cell Res. 2001, vol 10, pp. 75–79 discloses that inosine 5'-monophosphate and aspirin have an additive effect in resolving inflammatory response.

U.S. Pat. No. 6,060,459 to von Borstel et al. discloses using particular alky- or acyl-substituted inosine derivatives for treating inflammation diseases.

International Patent Publication No. WO 96/33203 discloses that inosine 5'-methylphosphate can reverse inflammation.

F. -H. Qui et al., *IMP and AMP Deaminase in Reperfusion Injury Down-Regulates Neutrophil Recruitment*, Proc. Natl. Acad. Sci. U.S.A., 2000, vol. 97, pp. 4267–4272 discloses that inosine can regulate neutrophils and play a role in inflammation and reperfusion.

M. P. Veerabagu et al., *Intravenous Nucleosides and a Nucleotide Promote Healing of Small Bowel Ulcers in Experimental Enterocolitis*, Digestive Diseases and Science 41, 1996, pp. 1452–1457 discloses the parenteral administration of a composition comprising inosine, cytidine, sodium 5'-guanylate, uridine and thymidine for the treatment bowel ulcers.

R. Norton et al., *Use of Nucleotides in Weanling Rats with Diarrhea Induced by a Lactose Overload: Effect on the Evolution of Diarrhea and Weight and on the Histopathology of Intestine, Liver, and Spleen*, Braz. J. Med. Biol. Res. 2001, vol. 34, pp. 195–202 discloses that a composition comprising inosine monophosphate, adenosine monophosphate, cytidine monophosphate, and uridine monophosphate improved the intestinal inflammatory response.

There remains, however, a clear need for compounds, compositions and methods that are useful for treating or preventing an inflammation disease, particularly inflammatory bowel disease, or a reperfusion disease.

Citation or identification of any reference in Section 2 of this application is not to be construed as our admission that such reference is prior art to the present application.

3. SUMMARY OF THE INVENTION

The invention relates to compounds of formula I:

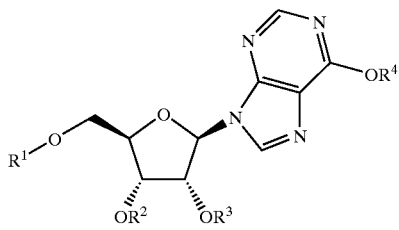

I and pharmaceutically acceptable salts thereof, wherein:

$R^1$ is $SO_3H$; and $R^2$, $R^3$ and $R^4$ are independently H, $C_2$–$C_6$ acyl, $PO_3H_2$, $P_2O_6H_3$ or $P_3O_9H_4$;

and at least one of $R^2$, $R^3$ and $R^4$ is not H.

The invention also relates to compounds of formula II:

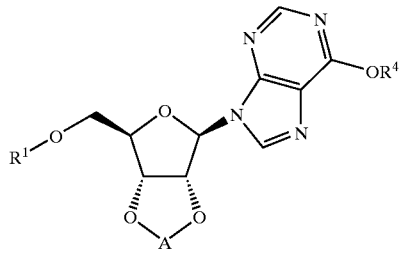

II and pharmaceutically acceptable salts thereof, wherein:

A is $-SO_2-$, $-C(O)-$ or $-P(O)OH$; and $R^1$ is $C_2$–$C_6$ acyl, $SO_3H$, $P_2O_6H_3$, or $P_3O_9H_4$; and $R^4$ is H, $C_2$–$C_6$ acyl, $SO_3H$, $PO_3H_2$, $P_2O_6H_3$ or $P_3O_9H_4$.

The compounds of formula I, the compounds of formula II, and pharmaceutically acceptable salts thereof, are useful for treating or preventing an inflammation disease or a reperfusion disease.

The invention also relates to compositions comprising a compound of formula I or a pharmaceutically acceptable salt thereof; and a pharmaceutically acceptable carrier. These compositions are useful for treating or preventing an inflammation disease or a reperfusion disease.

The invention also relates to compositions comprising a compound of formula II or a pharmaceutically acceptable salt thereof; and a pharmaceutically acceptable carrier. These compositions are useful for treating or preventing an inflammation disease or a reperfusion disease.

The invention further relates to methods for treating an inflammation disease comprising administering to a patient in need thereof an effective amount of a compound of formula I:

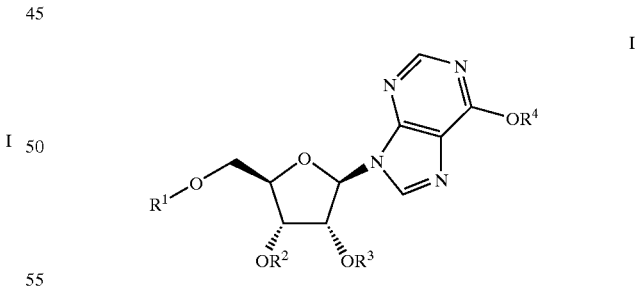

I or a pharmaceutically acceptable salt thereof, wherein:

$R^1$ is $C_2$–$C_6$ acyl, $SO_3H$ or $P_2O_6H_3$; and $R^2$, $R^3$ and $R^4$ are independently H, $C_2$–$C_6$ acyl, $SO_3H$, $PO_3H_2$, $P_2O_6H_3$ or $P_3O_9H_4$.

The invention further relates to methods for treating or preventing a reperfusion disease, comprising administering to a patient in need thereof an effective amount of a compound of formula I:

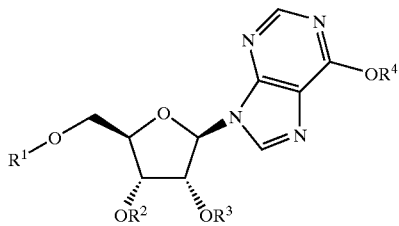

I or a pharmaceutically acceptable salt thereof, wherein:

$R^1$ is $C_2$–$C_6$ acyl, $SO_3H$, $P_2O_6H_3$ or $P_3O_9H_4$; and $R^2$, $R^3$ and $R^4$ are independently H, $C_2$–$C_6$ acyl, $SO_3H$, $PO_3H_2$, $P_2O_6H_3$ or $P_3O_9H_4$.

The invention further relates to methods for treating or preventing an inflammation disease, comprising administering to a patient in need thereof an effective amount of a compound of formula II:

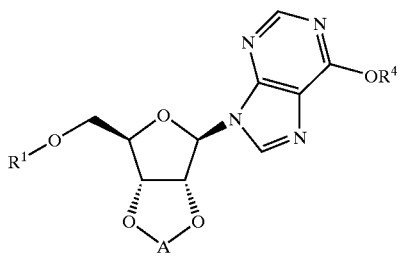

II or a pharmaceutically acceptable salt thereof, wherein:

A is —$SO_2$—, —C(O)— or —P(O)OH; and $R^1$ and $R^4$ are independently H, $C_2$–$C_6$ acyl, $SO_3H$, $PO_3H_2$, $P_2O_6H_3$ or $P_3O_9H_4$.

The invention further relates to methods for treating or preventing a reperfusion disease, comprising administering to a patient in need thereof an effective amount of a compound of formula II:

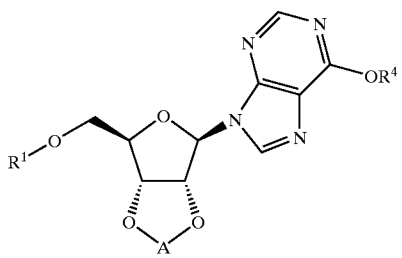

II or a pharmaceutically acceptable salt thereof, wherein:

A is —$S_2$—, —C(O)— or —P(O)OH; and $R^1$ and $R^4$ are independently H, $C_2$–$C_6$ acyl, $SO_3H$, $PO_3H_2$, $P_2O_6H_3$ or $P_3O_9H_4$.

The invention further relates to methods for treating or preventing an inflammation disease, comprising administering to a patient in need thereof an effective amount of a compound of formula III:

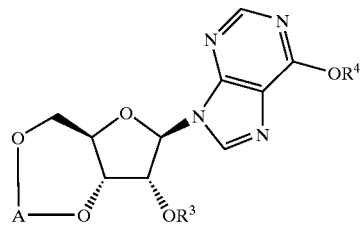

III or a pharmaceutically acceptable salt thereof, wherein:

A is —P(O)OH; and $R^3$ and $R^4$ are independently H, $C_2$–$C_6$ acyl, $SO_3H$, $PO_3H_2$, $P_2O_6H_3$ or $P_3O_9H_4$; and at least one of $R^3$ and $R^4$ is $C_2$–$C_6$ acyl, $SO_3H$, $PO_3H_2$, $P_2O_6H_3$ or $P_3O_9H_4$.

The invention further relates to methods for treating or preventing a reperfusion disease, comprising administering to a patient in need thereof an effective amount of a compound of formula III:

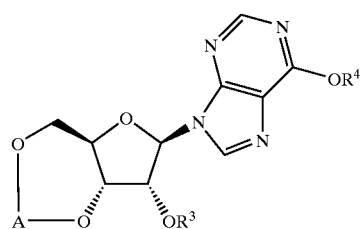

III or a pharmaceutically acceptable salt thereof, wherein:

A is —P(O)OH; and $R^3$ and $R^4$ are independently H, $C_2$–$C_6$ acyl, $SO_3H$, $PO_3H_2$, $P_2O_6H_3$ or $P_3O_9H_4$.

The invention further relates to methods for treating or preventing an inflammatory bowel disease, comprising administering to a patient in need thereof an effective amount of a compound of formula I:

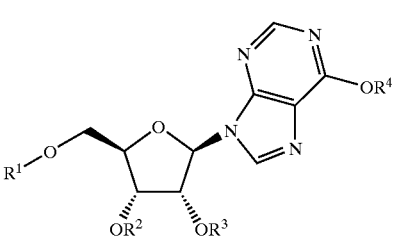

I or a pharmaceutically acceptable salt thereof, wherein:

$R^1$ is $C_2$–$C_6$ acyl, $SO_3H$, $PO_3H_2$, $P_2O_6H_3$ or $P_3O_9H_4$; and $R^2$, $R^3$ and $R^4$ are independently H, $C_2$–$C_6$ acyl, $SO_3H$, $PO_3H_2$, $P_2O_6H_3$ or $P_3O_9H_4$.

The invention also relates to methods for treating or preventing an inflammatory bowel disease, comprising administering to a patient in need thereof an effective amount of a composition consisting essentially of a compound of formula I:

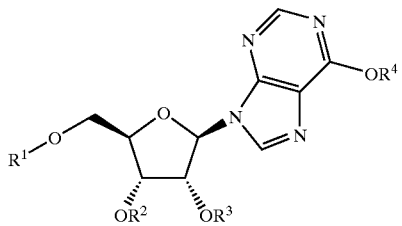

or a pharmaceutically acceptable salt thereof, wherein:

$R^1$, $R^2$, $R^3$ and $R^4$ are each independently H, $C_2$–$C_6$ acyl, $SO_3H$, $PO_3H_2$, $P_2O_6H_3$ or $P_3O_9H_4$.

The invention further relates to methods for treating or preventing an inflammatory bowel disease, comprising orally or enterally administering to a patient in need thereof an effective amount of a compound of formula I:

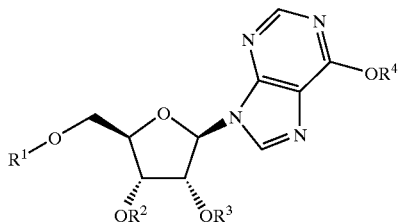

or a pharmaceutically acceptable salt thereof, wherein:

$R^1$, $R^2$, $R^3$ and $R^4$ are each independently H, $C_2$–$C_6$ acyl, $SO_3H$, $PO_3H_2$, $P_2O_6H_3$ or $P_3O_9H_4$.

The invention further relates to methods for treating or preventing an inflammatory bowel disease, comprising administering to a patient in need thereof an effective amount of a compound of formula II:

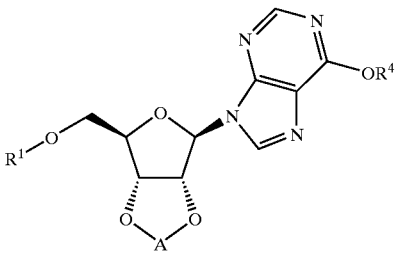

or, a pharmaceutically acceptable salt thereof, wherein:

A is —$SO_2$—, —$C(O)$— or —$P(O)OH$; and $R^1$ and $R^4$ are independently H, $C_2$–$C_6$ acyl, $SO_3H$, $PO_3H_2$, $P_2O_6H_3$ or $P_3O_9H_4$.

The invention further relates to methods for treating or preventing an inflammatory bowel disease, comprising administering to a patient in need thereof an effective amount of a compound of formula III:

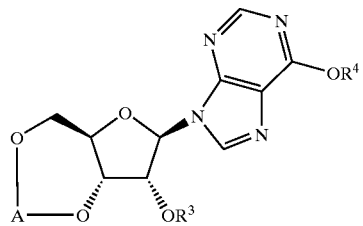

or, a pharmaceutically acceptable salt thereof, wherein:

A is —$P(O)OH$; and $R^3$ and $R^4$ are independently H, $C_2$–$C_6$ acyl, $SO_3H$, $PO_3H_2$, $P_2O_6H_3$ or $P_3H_4$.

The present invention may be understood more fully by reference to the following detailed description, figures and illustrative examples, which are intended to exemplify non-limiting embodiments of the invention.

4. BRIEF DESCRIPTION OF THE DRAWINGS

Figures 6A, 6B:
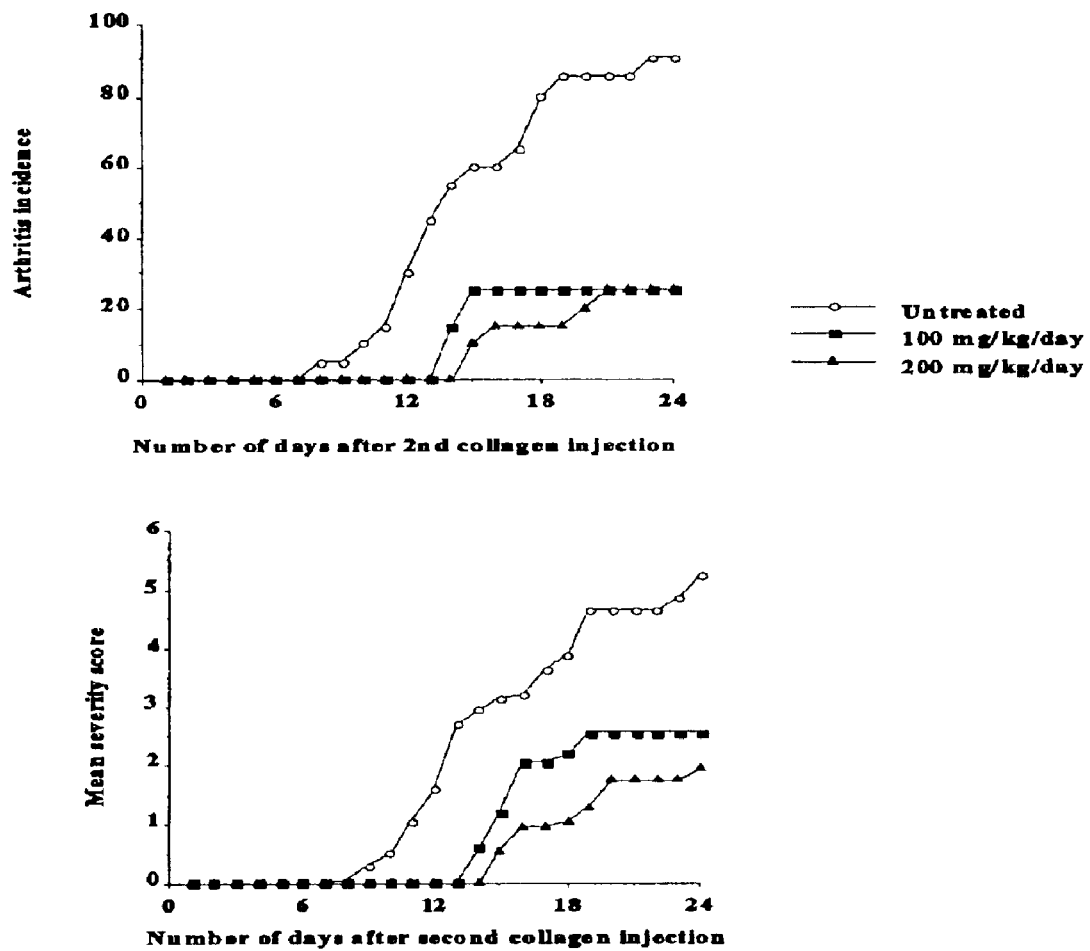

FIGS. 6A–B are graphs showing the effect of 5'-IMS on the incidence of arthritis in mice.

Figure 7:
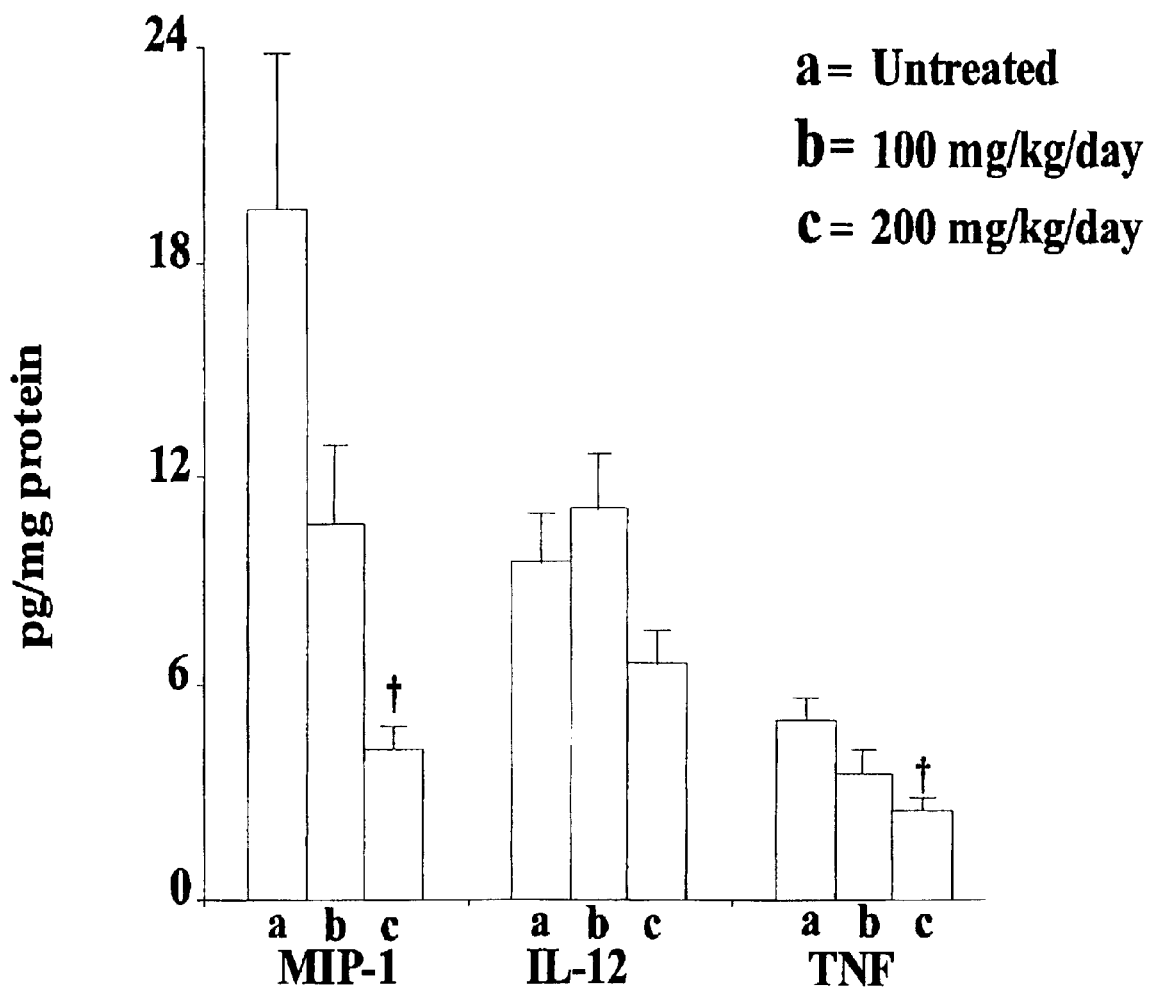

FIG. 7 is a graph showing the effect of 5'-IMS on the levels of the chemokine MIP-1α, and the cytokines IL-12 and TNF-α, in paws of DBA/1J mice treated with subdermal injections of collagen to induce arthritis.

Figures 8A, 8B:
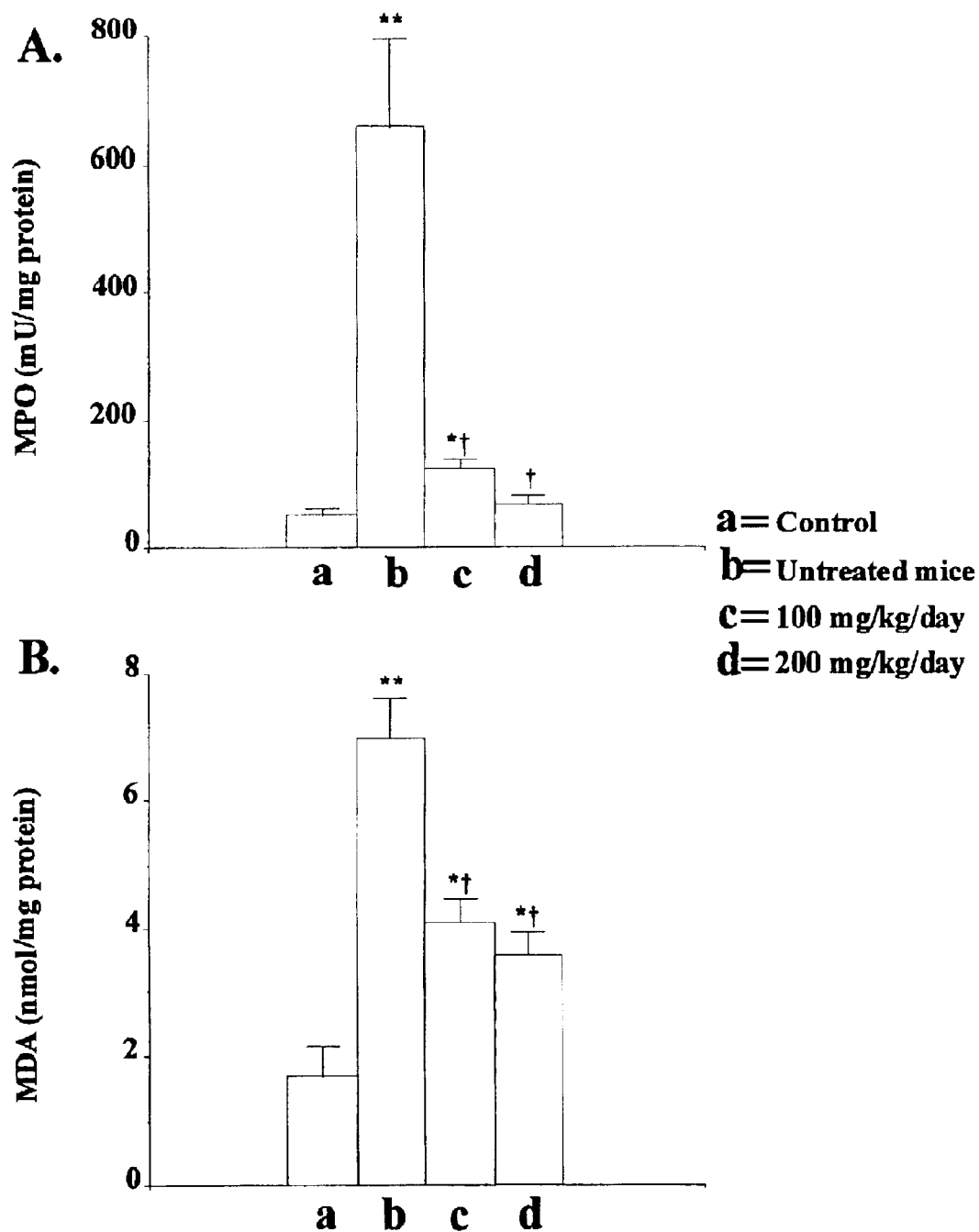

FIGS. 8A–8B are graphs showing the effect of 5'-IMS on the levels of (A) MPO and (B) MDA in paws of DBA/1J mice treated with subdermal injections of collagen to induce arthritis.

5. DETAILED DESCRIPTION OF THE INVENTION

5.1 Definitions

Examples of a "patient" are a mammal, e.g., a rat, mouse, rabbit, guinea pig, hamster, cow, pig, horse, goat, sheep, dog, cat, non-human primate, or human.

The phrase "pharmaceutically acceptable salt," as used herein is a salt formed from an acid and the basic nitrogen atom of one of the inosine compounds. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1-methylene-bis-(2-hydroxy-3-naphthoate)) salts. The term "pharmaceutically acceptable salt" also refers to a salt prepared from an inosine compound having an acidic functional group, such as a carboxylic, sulfuric or phosphoric acid functional group, and an inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl) amine, 2-hydroxy-tert-butylamine, or tris-(hydroxymethyl)methylamine, N, N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

Examples of "C1–C6" alkyl are methyl, ethyl, 1-propyl, 2-propyl, 1-butyl, 2-butyl, 2-methyl-2-propyl, 2-methyl-1-propyl, 1-pentyl, 1-methyl-1-butyl, 2-methyl-1-butyl, 3-methyl-1-butyl, 3-pentyl, 2-pentyl, 2,2-dimethyl-1-propyl, and 1-hexyl.

Examples of "C2–C6" acyl are acetyl, propanoyl, n-butanoyl, 2-methylpropanoyl, n-pentanoyl, 2-methylpropanoyl, 3-methylbutanoyl, 2,2-dimethylpropanoyl, n-hexanoyl, 2-methylpentanoyl, 3-methylpentanoyl, 4-methylpentanoyl, 2-ethylbutanoyl, 3,3-dimethybutanoyl and 2, 2-dimethylbutanoyl.

5.2 Compounds of Formula I and Formula II

As stated above, the present invention encompasses compounds of formula I:

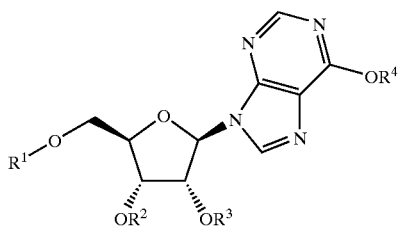

and pharmaceutically acceptable salts, thereof, where $R^1$ is $SO_3H$; and $R^2$, $R^3$ and $R^4$ are independently H, $C_2$–$C_6$ acyl, $PO_3H_2$, $P_2O_6H_3$ or $P_3O_9H_4$; and at least one of $R^2$, $R^3$ and $R^4$ is not H.

In one embodiment, the present invention encompasses compounds of formula I and pharmaceutically acceptable salts, thereof, where $R^1$ is $SO_3H$; and $R^2$, $R^3$ and $R^4$ are independently H, acyl, $PO_3H_2$, $P_2O_6H_3$or $P_3O_9H_4$; $R^4$ is H or $C_1$–$C_6$ alkyl; and at least one of $R^2$, $R^3$ and $R^4$ is not H. The invention also encompasses compounds of formula II:

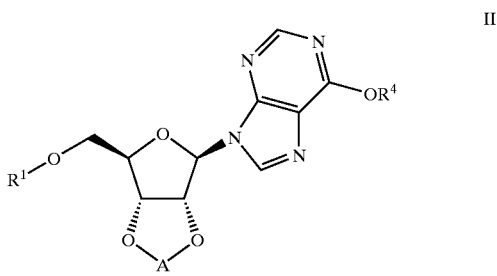

and pharmaceutically acceptable salts, thereof, where A is —$SO_2$—, —C(O)— or —P(O)OH; and $R^1$ is $C_2$–$C_6$ acyl, $SO_3H$, $P_2O_6H_3$, or $P_3O_9H_4$; and $R^4$ are independently H, $C_2$–$C_6$ acyl, $SO_3H$, $PO_3H_2$. $P_2O_6H_3$or $P_3O_9H_4$.

In one embodiment, invention also encompasses compounds of formula II and pharmaceutically acceptable salts, thereof, where A is —$SO_2$—, — or P(O)OH; $R^1$ is $C_2$–$C_6$ acyl, $SO_3H$, $P_2O_6H_3$, or $P_3O_9H_4$; and $R^4$ is H or $C_1$–$C_6$ alkyl.

The compounds of formula I and II can be obtained using conventional organic syntheses well known to those skilled in the art.

For example, the sulfate esters can be prepared by esterifying a hydroxyl of ionisine with $SO_3$ (See, e.g., sJ. March, *Advanced Organic Chemistry, Reaction Mechanisms and Structure*, 4th ed. John Wiley & Sons, 1992, p 404).

Inosine 5'-monophosphate can be prepared from inosine and pyrophosphoryl tetrachloride in acetonitrile (Netherlands Patent Publication No. NL 6610578).

Inosine 2',3'-cyclic phosphate can be prepared by reacting of 2',3'-O-isopropylideneinosine with $H_3PO_4$ and $Ac_2O$ followed by treatment with Amberlite IRA-401and with aqueous NaOH. (See e.g., JP 53044471 B.)

The sodium salts of inosine, inosine 3'-monophosphate, inosine 5'-diphosphate, inosine 5'-triphosphate, inosine 3',5'-cyclic monophosphate are commercially available (Sigma-Aldrich Chemical Co., Milwaukee, Wis.).

When preparing the compounds of formula I or II it may be necessary to protect one or more of the hydroxyls of inosine before forming the phosphate or sulfate group at another hydroxyl. It is possible to selectively esterify one of the hydroxyl groups of inosine. If one of the hydroxyl groups is more reactive than the other, the more reactive hydroxyl group can be selectively esterified. For example, the reactivity of the phenolic hydroxyl can be increased by deprotonating it to provide a more reactive phenoxide ion. The phenoxide ion is then selectively esterified. The phenolic hydroxyl can be easily deprotonated by reacting it with 1 equivalent of a base, such as lithium methoxide in methanol or sodium hydride.

A less reactive hydroxyl group can be selectively esterified by first reacting the more reactive hydroxyl group with a protecting group, esterifying the less reactive hydroxyl group, and then removing the protecting group. One skilled in the art would readily know how to selectively protect a hydroxyl group. For example, the phenolic hydroxyl can be selectively esterified by first deprotonating the phenolic hydroxyl to provide a more reactive phenoxide ion; reacting the phenoxide ion with a protecting group to provide a protected inosine, esterifying the less reactive hydroxyl of the protected ionisine, and then removing the protecting group. Suitable hydroxyl protecting groups include, but are not limited to, methyl ether, methoxymethyl ether, methoxythiomethyl ether, 2-methoxyethoxymethyl ether, bis(2-chloroethoxy)ethyl ether, tetrahydropyranyl ether, tetrahydrothiopyranyl ether, 4-methoxytetrahydropyranyl ether, methoxytetrahydrothiopyranyl ether, tetrahydrofuranyl ether, tetrahydrothiofuranyl ether, 1-ethoxyethyl ether, 1-methyl-1-methoxyethyl ether, 2-(phenylselenyl ether), t-butyl ether, allyl ether, benzyl ether, o-nitrobenzyl ether, triphenylmethyl ether, o-napthyldiphenylmethyl ether, p-methoxydiphenylmethyl ether, 9-(9-phenyl-10-oxo) anthryl ether (tritylone), trimethylsilyl ether, isopropyldimethylsilyl ether, t-butyldimethylsilyl ether, t-butyldiphenylsilyl ether, tribenzylsilyl ether, triisopropylsilyl ether, formate ester, acetate ester, trichloroacetate ester, phenoxyacetate ester, isobutyrate ester, pivaloate ester, adamantoate ester, benzoate ester, 2,4,6-trimethyl (mesitoate) ester, methyl carbonate, 2,2,2-trichlorocarbonate, allyl carbonate, p-nitrophenyl carbonate, benzyl carbonate, p-nitrobenzyl carbonate, S-benzylthiocarbonate, N-phenylcarbamate, nitrate ester, and 2,4-dinitrophenylsulfenate ester (See, e.g., T. W. Greene, *Protective Groups in Organic Synthesis*, John Wiley-Interscience Publication, New York, (1981)).

5.3 Composition

The invention also relates to pharmaceutical compositions comprising a compound of formula I:

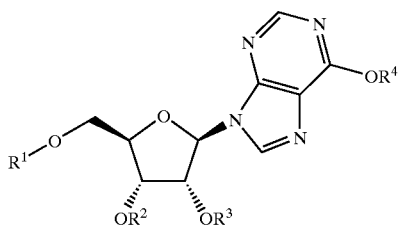

I or a pharmaceutically acceptable salt thereof, wherein:

$R^1$ is $SO_3H$; and $R^2$, $R^3$ and $R^4$ are independently H, $C_2$–$C_6$ acyl, $PO_3H_2$, $P_2O_6H_3$ or $P_3O_9H_4$;

at least one of $R^2$, $R^3$ and $R^4$ is not H; and a pharmaceutically acceptable carrier.

In one embodiment, the invention relates to pharmaceutical compositions comprising a compound of formula I where $R^1$ is $SO_3^{2-}$; $R^2$ and $R^3$ are independently H, $C_2$–$C_6$ acyl, $PO_3H_2$, $P_2O_6H_3$ or $P_3O_9H_4$; $R^4$ is H or $C_1$–$C_6$ alkyl; at least one of $R^2$, $R^3$ and $R^4$ is not H; and a pharmaceutically acceptable carrier.

The invention also relates to pharmaceutical compositions comprising a compound of formula II:

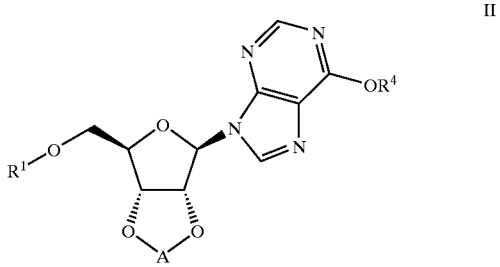

II or a pharmaceutically acceptable salt thereof, wherein:

A is $-SO_2-$, $-C(O)-$ or $-P(O)OH$;

$R^1$ is $C_2$–$C_6$ acyl, $SO_3H$, $P_2O_6H_3$. or $P_3O_9H_4$;

$R^4$ are independently H, $C_2$–$C_6$ acyl, $SO_3H$, $PO_3H_2$, $P_2O_6H_3$ or $P_3O_9H_4$; and a pharmaceutically acceptable carrier.

In one embodiment, the invention relates to pharmaceutical compositions comprising a compound of formula II or a pharmaceutically acceptable salt thereof, wherein A is $-SO_2-$, $-C(O)-$ or $-P(O)OH$; $R^1$ is $C^2$–$C^6$ acyl, $SO_3H$, $P_2O_6H_3$ or $P_3O_9H_4$; $R^4$ is H or $C_1$–$C_6$ alkyl; and a pharmaceutically acceptable carrier.

The invention also relates to pharmaceutical compositions comprising a compound of formula III

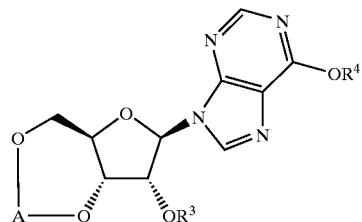

III or a pharmaceutically acceptable salt thereof, wherein:

A is $-P(O)OH$; and $R^3$ and $R^4$ are independently H, $C_2$–$C_6$ acyl, $SO_3H$, $P_3H_2$, $P_2O_6H_3$ or $P_3O_9H_4$;

at least one of $R^3$ and $R^4$ is $C_2$–$C_6$ acyl, $SO_3H$, $PO_3H_2$, $P_2O_6H_3$ or $P_3O_9H_4$; and a pharmaceutically acceptable carrier.

In one embodiment, the invention relates to pharmaceutical compositions comprising a compound of formula III or a pharmaceutically acceptable salt thereof, wherein A $-P(O)OH$; and $R^3$ is H, $C_2$–$C_6$ acyl, $SO_3H$, $PO_3H_2$, $P_2O_6H_3$ or $P_3O_9H_4$; $R^4$ is H or $C_1$–$C_6$ alkyl; and a pharmaceutically acceptable carrier.

5.4 Therapeutic Methods

The invention further provides compositions and methods and for treating disorders associated with the undesired secretion of macrophage inflammatory proteins. The invention is based in part on the observations that inosine compounds inhibit secretion of inflammatory cytokines and chemokines.

The invention is based in part on the discovery that inosine compounds inhibit the release of macrophage inflammatory proteins. Accordingly, the invention provides a method of treating a patient having or at risk for a condition associated with undesired secretion of a macrophage inflammatory protein. The method includes administering inosine compounds to a patient in need thereof.

In one aspect, the invention includes methods for treating a patient having, or at risk for, a condition associated with undesired secretion of a macrophage inflammatory protein (MIP). The method includes administering an inosine compound to the patient in an amount sufficient to treat or delay the onset of the condition.

The condition associated with undesired secretion of a MIP can be, e.g., inflammation, shock, or both. The inflammation can be associated with a condition such as e.g. diabetes mellitus (including autoimmune diabetes), adult respiratory distress syndrome, arthritis vasculitis, autoimmune disease, lupus erythematosus, ileitis, ulcerative colitis, Crohn's disease asthma, gingivitis, psoriasis, acne, periodontitis, ophthalmitis, endophthalmitis, nephrosis, AIDS-related neurodegeneration, stroke, neurotrauma, Alzheimer's disease, encephalomyelitis, cardiomyopathy, transplant rejection, and cancer.

Examples of conditions associated with shock include shock caused by, or associated with, gram positive bacteria-mediated circulatory shock, gram negative bacteria-mediated circulatory shock, hemorrhagic shock, anaphylactic shock, systemic inflammation, pro-inflammatory cytokines, and systemic inflammatory response syndrome (SIRS).

The immunomodulator can be administered via, e.g., intravenous, intramuscular, subcutaneous, topically, sublingual, oral, rectal, or aerosol delivery. Administration of the immunomodulator can be prophylactic, therapeutic, or both.

In a further aspect, the invention includes methods for treating or preventing diabetes, e.g., autoimmune diabetes, by administering to a patient in need of such treatment a safe and therapeutically effective amount of inosine, or an inosine receptor ligand, e.g., a compound which binds to an inosine binding site.

Also provided are methods for increasing insulin levels in a patient. The method includes administering to a patient in need thereof an amount of inosine or a ligand for an inosine binding site in an amount sufficient to increase insulin levels in said patient. In preferred embodiments, administering the inosine or inosine receptor ligand to the patient increases pancreatic insulin levels in the patient.

The methods and pharmaceutical compositions described herein can be used to inhibit or prevent secretion of inflammatory proteins such as TNF, IL-12, MIP-1α, and MIP-2. Because of the pivotal role of these proteins in the initiation and maintenance of inflammatory diseases, these cytokines are ideal targets for anti-inflammatory therapy in such disease states. The methods described herein can simultaneously inhibit release of multiple inflammatory proteins. Thus, because these inflammatory proteins act in distinct ways, higher therapeutic effectiveness can be obtained with the herein-described methods and compositions.

Accordingly, in one aspect, the invention provides methods for treating a patient having or at risk for a condition associated with undesired secretion of a macrophage inflammatory protein. By "at risk for" is meant a state that negatively impacts a patient such that they have an increased likelihood of developing a condition associated with undesired secretion of a macrophage inflammatory protein. "Undesired" as used herein is secretion of an inflammatory protein that causes, or is otherwise associated with, an undesired physiological reaction in the patient. Inflammatory proteins include proteins such as TNF, IL-12, MIP-1α, MIP-2, or IFN-γ.

In one aspect, the methods include administering to the patient an immunomodulator in an amount sufficient to treat, or delay the onset of, the condition. The immunomodulator preferably inhibits secretion of two or more macrophage inflammatory proteins. Alternatively, or in addition, the immunomodulator inhibits secretion of one or more macrophage inflammatory proteins while promoting expression of one or more anti-inflammatory proteins. An example of a macrophage anti-inflammatory protein is IL-10.

In some embodiments, an immunomodulator is used to treat or prevent diabetes mellitus in a patient. The diabetic condition can be, e.g., Type I or Type II diabetes. The diabetic condition treated can be autoimmune diabetes. Autoimmune diabetes is associated with a strong inflammatory component, activation of macrophages, and infiltration of mononuclear cells into the pancreas. The subsequent inflammatory processes bring about the deleterious consequences of inflammation diabetes, such as islet inflammation, islet cell destruction, insulin deficiency, and hyperglycemia. Rabinovitch et al., Biochem. Pharmacol. 55:1139–49, 1998; Almawi et al., J. Clin. Endocrinol. Metab. 84:1497–502, 1999. Macrophage-produced cytokines can be important mediators in the intraislet inflammatory processes. Accordingly, the herein-disclosed immunomodulators can be used to treat or prevent the development of a diabetic condition in a patient.

Also provided by the invention are methods for increasing inosine levels in a patient who has or is at risk of developing an inflammatory bowel disease. The method includes administering an amount of a compound of the invention (e.g., inosine, inosine adduct, or an analog of an inosine binding site) sufficient to increase inosine levels in the patient.

The invention also provides methods for treating or preventing an inflammation disease comprising administering to a patient in need thereof an effective amount of a compound of formula I:

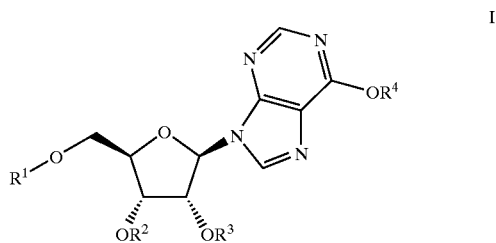

or a pharmaceutically acceptable salt thereof, where $R^1$ is $C_2$–$C_6$ acyl, $SO_3H$, $P_2O_6H_3$, and $R^2$, $R^3$ and $R^4$ are independently H, $C_2$–$C_6$ acyl, $SO_3H$, $PO_3H_2$, $P_2O_6H_3$ or $P_3O_9H_4$.

In one embodiment, the invention provides methods for treating or preventing an inflammation disease comprising administering to a patient in need thereof an effective amount of a compound of formula I or a pharmaceutically acceptable salt thereof where $R^1$ and $R^3$ are independently H, $C_2$–$C_6$ acyl, $SO_3H$, $PO_3H_2$, $P_2O_6H_3$ or $P_3O_9H_4$; $R^1$ is $C_2$–$C_6$ acyl or $SO_3H$; and $R^4$ H or $C_1$–$C_6$ alkyl.

The invention also provides methods for treating or preventing an inflammation disease comprising administering to a patient in need thereof an effective amount of a compound of formula I or a pharmaceutically acceptable salt thereof where $R^2$, $R^3$ and $R^4$ are independently H, $C_1$–$C_6$ acyl, $SO_3H$, $PO_3H_2$, $P_2O_6H_3$ or $P_3O_9H_4$; $R^1$ is $C_2$–$C_6$ acyl or $SO_3H$.

The invention also provides methods for treating or preventing an inflammation disease comprising administering to a patient in need thereof an effective amount of a compound of formula I or a pharmaceutically acceptable salt thereof where $R^2$, $R^3$ and $R^4$ are independently H, $C_2$–$C_6$ acyl, $SO_3H$, $PO_3H_2$, $P_2O_6H_3$ or $P_3O_9H_4$ and $R^1$ is $P_2O_6H_3$.

The invention also provides methods for treating or preventing an inflammation disease comprising administering to a patient in need thereof an effective amount of a compound of formula I or a pharmaceutically acceptable salt thereof where $R^2$, $R^3$ and $R^4$ are independently H, $C_2$–$C_6$ acyl, $SO_3H$, $PO_3H_2$, $P_2O_6H_3$ or $P_3O_9H_4$ and $R^1$ is $C_2$–$C_6$ acyl.

The invention also provides methods for treating or preventing an inflammation disease comprising administering to a patient in need thereof an effective amount of a compound of formula I or a pharmaceutically acceptable salt thereof where $R^2$, $R^3$ and $R^4$ are independently H, $C_2$–$C_6$ acyl, $SO_3H$, $PO_3H_2$, $P_2O_6H_3$ or $P_3O_9H_4$ and $R^1$ is acetyl.

The invention also provides methods for treating or preventing an inflammation disease comprising administering to a patient in need thereof any effective amount of a compound of formula II:

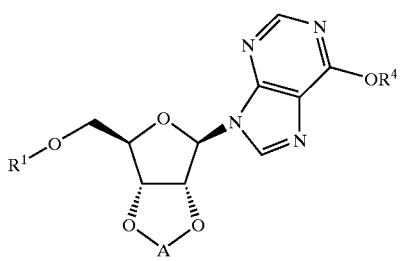

II or a pharmaceutically acceptable salt thereof, where A is —$SO_2$—, —C(O)— or —P(O)OH; and $R^1$ and $R^4$ independently are H, $C_2$–$C_6$ acyl, $SO_3H$, $PO_3H_2$, $P_2O_6H_3$ or $P_3O_9H_4$.

In one embodiment, the invention provides methods for treating or preventing an inflammation disease comprising administering to a patient in need thereof an effective amount of a compound of formula II or a pharmaceutically acceptable salt thereof A is —$SO_2$—, —C(O)— or —P(O)OH; and $R^1$ is H, $C_2$–$C_6$ acyl, $SO_3H$, $PO_3H_2$, $P_2O_6H_3$ or $P_3O_9H_4$; and $R^4$ is H or $C_1$–$C_6$ acyl.

The invention also provides methods for treating or preventing an inflammation disease comprising administering to a patient in need thereof an effective amount of a compound of formula II or a pharmaceutically acceptable salt thereof where A is —$SO_2$—, —C(O)— or —P(O)OH; and $R^4$ is H.

The invention also provides methods for treating or preventing an inflammation disease comprising administering to a patient in need thereof an effective amount of a compound of formula II or a pharmaceutically acceptable salt thereof where A is —$SO_2$—, $R^1$ is $SO_3H$ and $R^4$ H.

The invention also provides methods for treating or preventing an inflammation disease comprising administering to a patient in need thereof an effective amount of a compound of formula II or a pharmaceutically acceptable salt thereof where A is —$SO_2$—, —C(O)— or —P(O)OH; and $R^1$ and $R^4$ are H.

The invention also provides methods for treating or preventing an inflammation disease comprising administering to a patient in need thereof an effective amount of a compound of formula II or a pharmaceutically acceptable salt thereof where A is —P(O)OH; $R^1$ is $PO_3H_2$, $P_2O_6H_3$ or $P_3O_9H_4$; and $R^4$ is H.

The invention also provides methods for treating or preventing an inflammation disease comprising administering to a patient in need thereof an effective amount of a compound of formula II or a pharmaceutically acceptable salt thereof where A is —$SO_2$—, —C(O)— or —P(O)OH; and $R^1$ is $PO_3H_2$.

The invention also provides methods for treating or preventing an inflammation disease comprising administering to a patient in need thereof an effective amount of a compound of formula II or a pharmaceutically acceptable salt thereof where A is —$SO_2$—, —C(O)— or —P(O)OH; and $R^1$ is $P_2O_6H_3$.

The invention also provides methods for treating or preventing an inflammation disease comprising administering to a patient in need thereof an effective amount of a compound of formula II or a pharmaceutically acceptable salt thereof where A is —$SO_2$—, —C(O)— or —P(O)OH; and $R^1$ is $P_3O_3H_4$.

The invention further provides methods for treating or preventing an inflammation disease comprising administering to a patient in need thereof an effective amount of a compound of formula III:

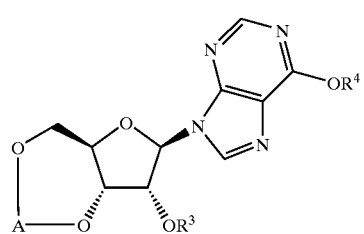

III or a pharmaceutically acceptable salt thereof, where A —P(O)OH; and $R^3$ and $R^4$ are independently are H, $C_2$–$C_6$ acyl, $SO_3H$, $PO_3H_2$, $P_2O_6H_3$ or $P_3O_9H_4$; and at least one of $R^3$ or $R^4$ is $C_2$–$C_6$ acyl, $SO_3H$, $PO_3H_2$, $P_2O_6H_3$ or $P_3O_9H_4$.

In one embodiment, the invention provides methods for treating or preventing an inflammation disease comprising administering to a patient in need thereof an effective amount of a compound of formula III or a pharmaceutically acceptable salt thereof where A is —P(O)OH; $R^3$ is H, $C_2$–$C_6$ acyl, $SO_3H$, $PO_3H_2$, $P_2O_6H_3$ or $P_3O_9H_4$; and $R^4$ is H or $C_1$–$C_6$ alkyl.

The invention further provides methods for treating or preventing an inflammation disease comprising administering to a patient in need thereof an effective amount of a compound of formula III or a pharmaceutically acceptable salt thereof where A is —$SO_2$—, —C(O)— or —P(O)OH; $R^3$ is $C_2$–$C_6$ acyl, $SO_3H$, $PO_3H_2$, $P_2O_6H_3$ or $P_3O_9H_4$ and $R^4$ is H.

Another embodiment of the invention is a method for treating or preventing a reperfusion disease comprising administering to a patient in need thereof a compound of formula I:

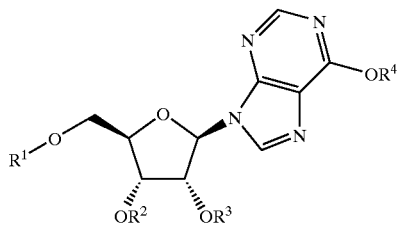

I or a pharmaceutically acceptable salts, thereof, where $R^1$ is $C_2$–$C_6$ acyl, $SO_3H$, $P_2O_6H_3$ or $P_3O_9H_4$; and $R^2$, $R^3$ and $R^4$ are independently H, $C_2$–$C_6$ acyl $SO_3H$, $PO_3H_2$, $P_2O_6H_3$ or $P_3O_9H_4$.

In one embodiment, the invention provides methods for treating or preventing a reperfusion disease comprising administering to a patient in need thereof an effective amount of a compound of formula I or a pharmaceutically acceptable salt thereof $R^1$ is $C_2$–$C_6$ acyl, $SO_3H$, $P_2O_6H_3$ or $P_3O_9H_4$; and $R^2$ and $R^3$ are independently H, $C_2$–$C_6$ acyl, $SO_3H$, $PO_3H_2$, $P_2O_6H_3$ or $P_3O_9H_4$; and $R^4$ is H or $C_1$–$C_6$ alkyl.

The invention also provides methods for treating or preventing a reperfusion disease comprising administering to a patient in need thereof an effective amount of a compound of formula I or a pharmaceutically acceptable salt thereof where $R^1$ is $C_2$–$C_6$ acyl, $SO_3H$, $P_2O_6H_3$ or $P_3O_9H_4$; and $R^2$, $R^3$ and $R^4$ are independently H.

The invention also provides methods for treating or preventing a reperfusion disease comprising administering to a patient in need thereof an effective amount of a compound of formula I or a pharmaceutically acceptable salt thereof where $R^2$, $R^3$ and $R^4$ are independently H, $C_2$–$C_6$ acyl, $SO_3H$, $PO_3H_2$, $P_2O_6H_3$, or $P_3O_9H_4$; and $R^1$ is $SO_3H$.

The invention also provides methods for treating or preventing a reperfusion disease comprising administering to a patient in need thereof an effective amount of a compound of formula I or a pharmaceutically acceptable salt thereof where $R^2$, $R^3$ and $R^4$ are independently H, $C_2$–$C_6$ acyl, $SO_3H$, $PO_3H_2$, $P_2O_6H_3$, or $P_3O_9H_4$; and $R^1$ is $P_2O_6H_3$.

The invention also provides methods for treating or preventing a reperfusion disease comprising administering to a patient in need thereof an effective amount of a compound of formula I or a pharmaceutically acceptable salt thereof where $R^2$, $R^3$ and $R^4$ are independently H, $C_2$–$C_6$ acyl, $SO_3H$, $PO_3H_2$, $P_2O_6H_3$, or $P_3O_9H_4$; and $R^1$ is $P_3O_9H_4$.

The invention also provides methods for treating or preventing a reperfusion disease comprising administering to a patient in need thereof an effective amount of a compound of formula I or a pharmaceutically acceptable salt thereof where $R^2$, $R^3$ and $R^4$ are independently H, $C_2$–$C_6$ acyl, $SO_3H$, $PO_3H_2$, $P_2O_6H_3$, or $P_3O_9H_4$; and $R^1$ is $C_2$–$C_6$ acyl.

The invention also provides methods for treating or preventing a reperfusion disease comprising administering to a patient in need thereof an effective amount of a compound of formula I or a pharmaceutically acceptable salt thereof where $R^2$, $R^3$ and $R^4$ are independently H, $C_2$–$C_6$ acyl, $SO_3H$, $PO_3H_2$, $P_2O_6H_3$, or $P_3O_9H_4$; and $R^1$ is acetyl.

Another embodiment of the invention is a method for treating or preventing a reperfusion disease comprising administering to a patient in need thereof an effective amount of a compound of formula II:

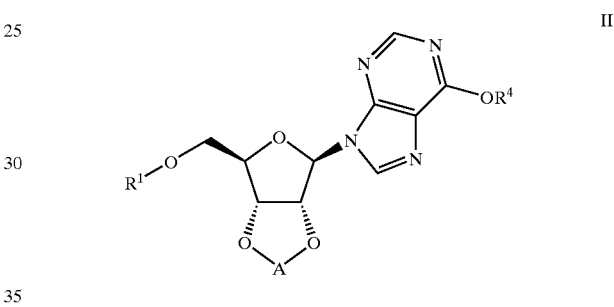

II or a pharmaceutically acceptable salt, thereof, where A is —$SO_2$—, —C(O)— or —P(O)OH; and $R^1$ and $R^4$ independently are H, $C_2$–$C_6$ acyl, $SO_3H$, $PO_3H_2$, $P_2O_6H_3$, or $P_3O_9H_4$.

In one embodiment, the invention provides methods for treating or preventing a reperfusion disease comprising administering to a patient in need thereof an effective amount of a compound of formula II or a pharmaceutically acceptable salt thereof A is —$SO_2$—, —C(O)— or —P(O)OH; $R^{is\ 1}$ is H, $C_2$–$C_6$acyl, $SO_3H$, $PO_3H_2$, $P_2O_6H_3$, or $P_3O_9H_4$; and $R^4$ is H or $C_1$–$C_6$alkyl.

The invention also provides methods for treating or preventing a reperfusion disease comprising administering to a patient in need thereof an effective amount of a compound of formula II or a pharmaceutically acceptable salt thereof where A is —$SO_2$—, —C(O)— or —P(O)OH, and $R^4$ is H.

The invention also provides methods for treating or preventing a reperfusion disease comprising administering to a patient in need thereof an effective amount of a compound of formula II or a pharmaceutically acceptable salt thereof where A is —$SO_2$—, —C(O)— or —P(O)OH, and $R^1$ and $R^4$ are H.

The invention also provides methods for treating or preventing a reperfusion disease comprising administering to a patient in need thereof an effective amount of a compound of formula II or a pharmaceutically acceptable salt thereof where A is —$SO_2$—, $R^1$ is $SO_3H$; and $R^4$ is H.

The invention also provides methods for treating or preventing a reperfusion disease comprising administering to a patient in need thereof an effective amount of a compound of formula II or a pharmaceutically acceptable salt thereof where A is —P(O)OH, and $R^1$ is $PO_3H_2$, $P_2O_6H_3$ or $P_3O_9H_4$ and $R^4$ is H.

The invention also provides methods for treating or preventing a reperfusion disease comprising administering to a patient in need thereof an effective amount of a compound of formula II or a pharmaceutically acceptable salt thereof where A is —$SO_2$—, —C(O)— or —P(O)OH; and $R^1$ is $P_2O_6H_2$.

The invention also provides methods for treating or preventing a reperfusion disease comprising administering to a patient in need thereof an effective amount of a compound of formula II or a pharmaceutically acceptable salt thereof where A is —$SO_2$—, —C(O)— or —P(O)OH; and $R^1$ is $P_2O_6H_3$.

The invention also provides methods for treating or preventing a reperfusion disease comprising administering to a patient in need thereof an effective amount of a compound of formula II or a pharmaceutically acceptable salt thereof where A is —$SO_2$—, —C(O)— or —P(O)OH; and $R^1$ is $P_3O_9H_4$.

Another embodiment of the invention is a method for treating and preventing a reperfusion disease comprising administering to a patient in need thereof an effective amount of a compound of formula III:

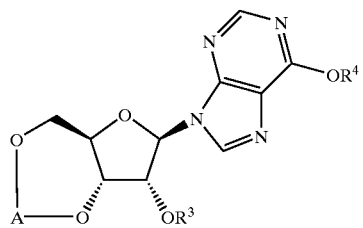

III or a pharmaceutically acceptable salt thereof, where A is —P(O)OH; and $R^3$ and $R^4$ independently are H, $C_2$–$C_6$ acyl, $SO_3H$, $PO_3H_2$, $P_2O_6H_3$ or $P_3O_9H_4$.

In one embodiment, the invention provides methods for treating or preventing a reperfusion disease comprising administering to a patient in need thereof an effective amount of a compound of formula III or a pharmaceutically acceptable salt thereof A is —P(O)OH; $R^3$ is H, $C_2$–$C_6$ acyl, $SO_3H$, $PO_3H_2$, $P_2O_6H_3$ or $P_3O_9H_4$; and $R^4$ is H or $C_1$–$C_6$ alkyl.

The invention also provides methods for treating or preventing a reperfusion disease comprising administering to a patient in need thereof an effective amount of a compound of formula III or a pharmaceutically acceptable salt thereof where A is —$SO_2$—, —C(O)— or —P(O)OH; and $R^3$ is $C_2$–$C_6$ acyl, $SO_3H$, $PO_3H_2$, $P_2O_6H_3$ and $R^4$ is H.

The invention also provides methods for treating or preventing a reperfusion disease comprising administering to a patient in need thereof an effective amount of a compound of formula III or a pharmaceutically acceptable salt thereof where A is —$SO_2$—, —C(O)— or —P(O)OH; and $R^3$ and $R^4$ are H.

Another embodiment of the invention is a method for treating or preventing an inflammatory bowel disease comprising administering to a patient in need thereof a compound of formula I:

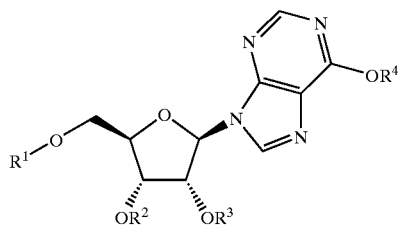

I or a pharmaceutically acceptable salt thereof, where $R^1$ is $C_2$–$C_6$ acyl, or $SO_3H$, $PO_3H_2$, $P_2O_6H_3$ or $P_3O_9H_4$; and $R^2$, $R^3$ and $R^4$ are independently H, $C_2$–$C_6$ acyl, $SO_3H$, $PO_3H_2$, $P_2O_6H_3$ or $P_3O_9H_4$.

In one embodiment, the invention provides methods for treating or preventing an inflammatory bowel disease comprising administering to a patient in need thereof an effective amount of a compound of formula I or a pharmaceutically acceptable salt thereof where $R^1$ is $C_2$–$C_6$ acyl, $SO_3H$, $PO_3H_2$, $P_2O_6H_3$ or $P_3O_9H_4$; $R^2$ and $R^3$ are independently H, $C_2$–$C_6$ acyl, $SO_3H$, $PO_3H_2$, $P_2O_6H_3$ or $P_3O_9H_4$; and $R^4$ is H or $C_1$–$C_6$ alkyl.

The invention also provides methods for treating or preventing an inflammatory bowel disease comprising administering to a patient in need thereof an effective amount of a compound of formula I or a pharmaceutically acceptable salt thereof where $R^1$ is $SO_3H$ and $R^2$, $R^3$ and $R^4$ are H.

The invention also provides methods for treating or preventing an inflammatory bowel disease comprising administering to a patient in need thereof an effective amount of a compound of formula I or a pharmaceutically acceptable salt thereof where $R^1$ is $P_3H_2$ and $R^2$, $R^3$ and $R^4$ are H.

The invention also provides methods for treating or preventing an inflammatory bowel disease comprising administering to a patient in need thereof an effective amount of a compound of formula I or a pharmaceutically acceptable salt thereof $R^1$ is $P_2O_6H_3$ and $R^2$, $R^3$ and $R^4$ are H.

The invention also provides methods for treating or preventing an inflammatory bowel disease comprising administering to a patient in need thereof an effective amount of a compound of formula I or a pharmaceutically acceptable salt thereof where $R^1$ is $P_3O_9H_4$ and $R^2$, $R^3$ and $R^4$ are H.

The invention also provides methods for treating or preventing an inflammatory bowel disease comprising administering to a patient in need thereof an effective amount of a compound of formula I or a pharmaceutically acceptable salt thereof where $R^1$ is acyl and $R^2$, $R^3$ and $R^4$ are H.

The invention also provides methods for treating or preventing an inflammatory bowel disease comprising administering to a patient in need thereof an effective amount of a composition consisting essentially of an effective amount of a compound of formula I:

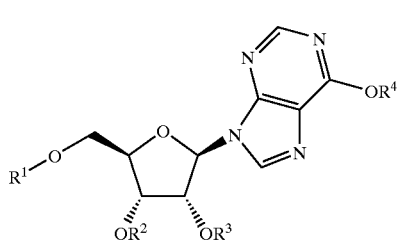

or a pharmaceutically acceptable salt thereof, wherein:
$R^1$, $R^2$, $R^3$ and $R^4$ are independently H, $C_2$–$C_6$ acyl, $SO_3H$, $PO_3H_2$, $P_2O_6H_3$ or $P_3O_9H_4$.

In one embodiment, the invention provides methods for treating or preventing an inflammatory bowel disease, comprising administering to a patient in need thereof a composition consisting essentially of an effective amount of a compound of formula I, or a pharmaceutically acceptable salt thereof, wherein $R^1$, $R^2$ and $R^3$ are each independently H, $C_2$–$C_6$ acyl, $SO_3H$, $PO_3H_2$, $P_2O_6H_3$ or $P_3O_9H_4$; and $R^4$ is H or $C_1$–$C_6$ alkyl.

The invention also provides methods for treating or preventing an inflammatory bowel disease, comprising administering to a patient in need thereof a composition consisting essentially of an effective amount of a compound of formula I, or a pharmaceutically acceptable salt thereof, wherein $R^1$, $R^2$, $R^3$ and $R^4$ are H.

The invention also provides methods for treating or preventing an inflammatory bowel disease, comprising administering to a patient in need thereof a composition consisting essentially of an effective amount of a compound of formula I, or a pharmaceutically acceptable salt thereof, wherein $R^1$ is $SO_3H$; and $R^2$, $R^3$ and $R^4$ are H.

The invention also provides methods for treating or preventing an inflammatory bowel disease, comprising administering to a patient in need thereof a composition consisting essentially of an effective amount of a compound of formula I, or a pharmaceutically acceptable salt thereof, wherein $R^1$ is $PO_3H_2$; and $R^2$, $R^3$ and $R^4$ are H.

The invention also provides methods for treating or preventing an inflammatory bowel disease, comprising administering to a patient in need thereof a composition consisting essentially of an effective amount of a compound of formula I, or a pharmaceutically acceptable salt thereof, wherein $R^1$ is $P_2O_6H_3$; and $R^2$, $R^3$ and $R^4$ are H.

The invention also provides methods for treating or preventing an inflammatory bowel disease, comprising administering to a patient in need thereof a composition consisting essentially of an effective amount of a compound of formula I, or a pharmaceutically acceptable salt thereof, wherein $R^1$ is $P_3O_9H_4$; and $R^2$, $R^3$ and $R^4$ are H.

The invention also provides methods for treating or preventing an inflammatory bowel disease, comprising administering to a patient in need thereof a composition consisting essentially of an effective amount of a compound of formula I, or a pharmaceutically acceptable salt thereof, wherein $R^1$ is a $C_2$–$C_6$ acyl; and $R^2$, $R^3$ and $R^4$ are H.

The invention also provides methods for treating or preventing an inflammatory bowel disease comprising orally or enterally administering to a patient in need thereof an effective amount of a compound of formula I:

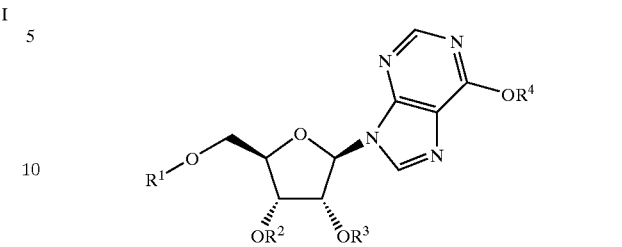

or a pharmaceutically acceptable salt thereof, wherein $R^1$, $R^2$, $R^3$ and $R^4$ are each independently H, $C_2$–$C_6$ acyl, $SO_3H$, $PO_3H_2$, $P_2O_6H_3$ or $P_3O_9H_4$.

In one embodiment, the invention provides methods for preventing or treating an inflammatory bowel disease, comprising orally or enterally administering to a patient in need thereof an effective amount of a compound of formula I or a pharmaceutically acceptable salt thereof wherein $R^1$, $R^2$ and $R^3$ are each independently H, $C_2$–$C_6$ acyl, $SO_3H$, $PO_3H_2$, $P_2O_6H_3$ or $P_3O_9H_4$; and $R^4$ is H or $C_1$–$C_6$ alkyl.

The invention also provides methods for preventing or treating an inflammatory bowel disease, comprising orally or enterally administering to a patient in need thereof an effective amount of a compound of formula I or a pharmaceutically acceptable salt thereof where $R^1$, $R^2$, $R^3$ and $R^4$ are H.

The invention also provides methods for preventing or treating an inflammatory bowel disease, comprising orally or enterally administering to a patient in need thereof an effective amount of a compound of formula I or a pharmaceutically acceptable salt thereof where $R^1$ is $SO_3H$ and $R^2$, $R^3$ and $R^4$ are H.

The invention also provides methods for preventing or treating an inflammatory bowel disease, comprising orally or enterally administering to a patient in need thereof an effective amount of a compound of formula I or a pharmaceutically acceptable salt thereof where $R^1$ is $PO_3H_2$; and $R^2$, $R^3$ and $R^4$ are H.

The invention also provides methods for preventing or treating an inflammatory bowel disease, comprising orally or enterally administering to a patient in need thereof an effective amount of a compound of formula I or a pharmaceutically acceptable salt thereof where $R^1$ is $P_2O_6H_3$; and $R^2$ $R^3$ and $R^4$ are H.

The invention also provides methods for preventing or treating an inflammatory bowel disease, comprising orally or enterally administering to a patient in need thereof an effective amount of a compound of formula I or a pharmaceutically acceptable salt thereof where $R^1$ is $P_3O_9H_4$, and $R^2$, $R^3$ and $R^4$ are H.

The invention also provides methods for preventing or treating an inflammatory bowel disease, comprising orally or enterally administering to a patient in need thereof an effective amount of a compound of formula I or a pharmaceutically acceptable salt thereof where $R^1$ is a $C_2$–$C_6$ acyl; and $R^2$, $R^3$ and $R^4$ are H.

Another embodiment of the invention is a method for treating or preventing an inflammatory bowel disease, comprising administering to a patient in need thereof an effective amount of a compound of formula II:

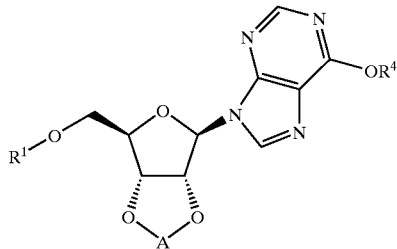

II or a pharmaceutically acceptable salt thereof, wherein:
A is —$SO_2$—, —C(O)— or —P(O)OH; and
$R^1$ and $R^4$ independently are H, $C_2$–$C_6$ acyl, $SO_3H$, $PO_3H_2$, $P_2O_6H_3$ or $P_3O_9H_4$.

In one embodiment, the invention provides methods for treating or preventing an inflammatory bowel disease comprising administering to a patient in need thereof an effective amount of a compound of formula II or a pharmaceutically acceptable salt thereof where A is —$SO_2$—, —C(O)— or —P(O)OH, $R^1$ is H, $C_2$–$C_6$ acyl, $SO_3H$, $PO_3H_2$, $P_2O_6H_3$ or $P_3O_9H_4$; and $R^4$ is H or $C_1$–$C_6$ alkyl.

The invention also provides methods for treating or preventing an inflammatory bowel disease comprising administering to a patient in need thereof an effective amount of a compound of formula II or a pharmaceutically acceptable salt thereof where is —$SO_2$—, —C(O)— or —P(O)OH, and $R^1$ is H, $C_2$–$C_6$ acyl, $SO_3H$, $PO_3H_2$, $P_2O_6H_3$ or $P_3O_9H_4$ and $R^4$ H.

The invention also provides methods for treating or preventing an inflammatory bowel disease comprising administering to a patient in need thereof are effective amount of a compound of formula II or a pharmaceutically acceptable salt thereof where A is —$SO_2$—, —C(O)— or —P(O)OH, and $R^1$ and $R^4$ is H.

The invention also provides methods for treating or preventing an inflammatory bowel disease comprising administering to a patient in need thereof an effective amount of a compound of formula II or a pharmaceutically acceptable salt thereof where A is —$SO_2$—, $R^1$ is $SO_3$ and $R^4$ is H.

The invention also provides methods for treating or preventing an inflammatory bowel disease comprising administering to a patient in need thereof an effective amount of a compound of formula II or a pharmaceutically acceptable salt thereof where A —P(O)OH; $R^1$ is $PO_3H_2$, $P_2O_6H_3$ or $P_3O_9H_4$ and $R^4$ is H.

The invention also provides methods for treating or preventing an inflammatory bowel disease comprising administering to a patient in need thereof an effective amount of a compound of formula II or a pharmaceutically acceptable salt thereof where A is —$SO_2$—, —C(O)— or —P(O)OH; and $R^1$ is $P_2O_6H_3$.

The invention also provides methods for treating or preventing an inflammatory bowel disease comprising administering to a patient in need thereof an effective amount of a compound of formula II or a pharmaceutically acceptable salt thereof A is —$SO_2$—, —C(O)— or —P(O) OH; and $R^1$ $P_2O_6H_3$.

The invention also provides methods for treating or preventing an inflammatory bowel disease comprising administering to a patient in need thereof an effective amount of a compound of formula II or a pharmaceutically acceptable salt thereof where is —$SO_2$—, —C(O)— or —P(O)OH; and $R^1$ is $P_3O_9H_4$.

Another embodiment of the invention is a method for treating or preventing an inflammatory bowel disease, comprising administering to a patient in need thereof an effective amount of a compound of formula III:

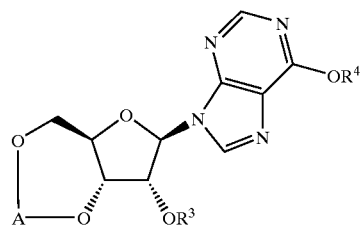

III or a pharmaceutically acceptable salt thereof, wherein:
A is —P(O)OH; and
$R^3$ and $R^4$ are independently H, $C_2$–$C_6$ acyl, $SO_3H$, $PO_3H_2$, $P_2O_6H_3$ or $P_3O_9H_4$.

In one embodiment, the invention provides methods for treating or preventing an inflammatory bowel disease comprising administering to a patient in need thereof an effective amount of a compound of formula III or a pharmaceutically acceptable salt thereof A is —P(O)OH; $R^3$ is H, $C_2$–$C_6$ acyl, $SO_3H$, $PO_3H_2$, $P_2O_6H_3$ or $P_3O_9H_4$; and $R^4$ H or $C_1$–$C_6$ alkyl.

The invention also provides methods for treating or preventing an inflammatory bowel disease comprising administering to a patient in need thereof an effective amount of a compound of formula III or a pharmaceutically acceptable salt thereof where A —P(O)OH; $R^3$ is $C_2$–$C_6$ acyl, $SO_3H$, $PO_3H_2$, $P_2O_6H_3$ or $P_3O_9H_4$; and $R^4$ is H.

The invention also provides methods for treating or preventing an inflammatory bowel disease comprising administering to a patient in need thereof an effective amount of a compound of formula III or a pharmaceutically acceptable salt thereof where A is —P(O)OH; and $R^3$ and $R^4$ are H.

The compounds of formulas I–III and pharmaceutically acceptable salts thereof (collectively, the "inosine compounds") are useful for treating or preventing an inflammation disease or a reperfusion disease.

The preferred compounds of the present methods are compounds of formula I where:
$R^1$, $R^2$, $R^3$ and $R^4$ are H (also known as inosine);
$R^1$ is $SO_3^-$, and $R^2$, $R^3$ and $R^4$ are H (also known as inosine 5'-monosulfate);
$R^1$ is $PO_3^{2-}$, and $R^2$, $R^3$ and $R^4$ are H (also known as inosine 5'-monophosphate);
$R^1$ is $P_2O_6^{3-}$, and $R^2$, $R^3$ and $R^4$ are H (also known as inosine 5'-diphosphate);
$R^1$ is $P_3O_9^{4-}$, and $R^2$, $R^3$ and $R^4$ are H (also known as inosine 5-triphosphate); and
pharmaceutically acceptable salts thereof.

Examples of inflammation diseases include chronic inflammatory disorders of the joints including arthritis, e.g., rheumatoid arthritis and osteoarthritis; inflammatory bowel diseases such as ileitis, ulcerative colitis and Crohn's disease; and inflammatory lung disorders such as asthma and chronic obstructive airway disease. Other examples of inflammation diseases include inflammatory disorders of the eye such as corneal dystrophy, trachoma, onchocerciasis, uveitis, sympathetic ophthalmitis, and endophthalmitis. Inflammation diseases also include chronic inflammatory disorders of the gum, e.g., periodontitis; tuberculosis; leprosy; inflammatory diseases of the kidney including glomerulonephritis and nephrosis; inflammatory disorders of the skin including acne, sclerodermatitis, psoriasis, eczema, photoaging and wrinkles; inflammatory diseases of the central nervous system, including AIDS-related neurodegeneration, stroke, neurotraua and Alzheimer's disease, encephalomyelitis and viral or autoimmune encephalitis; autoimmune diseases including immune-complex vasculitis, systemic lupus and erythematodes; systemic lupus erythematosus (SLE); and inflammatory diseases of the heart such as cardiomyopathy. Additional examples include adult respiratory distress syndrome, gingivitis, transplant rejection, and cancer.

Examples of reperfusion disease include shock and sepsis. Shock in the patient may be associated with an underlying condition such as septic shock, e.g., gram positive bacteria-mediated circulatory shock, gram negative bacteria-mediated circulatory shock, hemorrhagic shock, anaphylactic shock, systemic inflammation, pro-inflammatory cytokines, and systemic inflammatory response syndrome (SIRS). The inosine compounds can also be used to prevent or treat circulatory shock, such as shock occurring as a result of gram negative and gram positive sepsis, trauma, hemorrhage, burn injury, anaphylaxis, cytokine immunotherapy, liver failure, kidney failure or systemic inflammatory response syndrome.

Other examples of reperfusion disease are disease arising from solid organ transplantation, cardiopulmonary bypass surgery, compartment syndrome, crush injury, splanchnic ischemia-reperfusion, myocardial infarction and stroke.

In another aspect, the invention provides pharmaceutical compositions comprising one or more of the herein-described immunomodulators. The compositions can be used for treating a patient having or at risk for a condition associated with undesired secretion of the macrophage inflammatory protein. As used herein, an "immunomodulator" is a compound that modulates an immune response by inhibiting expression or activity of one or more macrophage inflammatory proteins. Expression can be inhibited, for example, by inhibiting secretion of the inflammatory proteins. Examples of immunomodulators include inosine compounds.

An immunomodulator of the invention can also be provided as an inosine compound. Inosine compounds include inosine, inosine analogs, inosine prodrugs, and inosine adducts.

Examples of inosine analogs include, e.g., 8-bromoinosine, and 8-chloroinosine. Inosine analogs include those which bind to an inosine binding site, or are inosine receptor ligands.

The inosine compounds can be administered therapeutically or prophylactically and can be administered in any route recognized in the art. For example, administration can be intravenous, intramuscular, subcutaneous, sublingual, oral, enteral, rectal or by aerosol delivery. In some embodiments, the inosine compounds are administered to the patient in the form of a depot. Preferably, the depot increases the biological half-life of the compound of the invention.

Administration can be at a dose from about 0.1 to about 500 mg/kg/day of the inosine compound to the patient. In various embodiments, the dose is, e.g., between about 0.5 to 250 mg/kg/day, 1.0 to 125 mg/kg/day, 5 to 75 mg/kg/day, 10 to 50 mg/kg/day, or 20 to 40 mg/kg/day.

If desired, inosine compounds, can be administered along with a second agent that itself is useful for treating or preventing a condition associated with an inflammation disease or a reperfusion disease. For example, the second agent can be an antibiotic, a glucocorticoid, an immunosuppressive agent, an aminosalicylate, and a non-steroidal anti-inflammatory agent. Examples of second agents include, e.g., dexamethasone, 5-aminosalicylic acid, sulfasalazine, 4-aminosalicylic acid, sulphapyridine, 6-mercaptopurine, azathioprine, cyclosporine, anti-tumor necrosis factor antibody, soluble tumor necrosis factor receptor, and an anti-CS antibody. If desired, the inosine compounds can be administered along with two or more, e.g., three, four, or five of the second agents.

In another aspect, the invention includes compositions comprising an effective amount of an inosine compound and a pharmaceutically effective carrier. Preferably, the composition is useful formulated for treating or preventing an inflammatory bowel disease in a patient. For example, the compositions can include one or more of a pharmacologically- and bowel-compatible carrier, adapted for delivery of the inosine compound to the bowel of the patient. Any carrier recognized in the art can be used. Examples of carriers include, (i) a foam suitable for rectal administration; (ii) a suppository base which surrounds the compound of the invention; and (iii) an orally ingestible time-release substance which withstands degradation by the gastric acids of the stomach and releases the compound in the bowel. The composition can be administered as an enema.

The inosine compounds can be present in the compositions an amount ranging from, e.g., about 0.01 grams to about 20 grams.

Where the composition comprises a foam, the foam preferably comprises an inosine compound, a surfactant, an adjuvant and a blowing agent. For example, the foam can include 0.5 to 5 grams of an inosine compound and 20 g of a foam comprising propylene glycol, emulsifying wax, polyoxyethylene-10-stearyl ether, cetyl alcohol, methylparaben and propylparaben, trolamine, purified water and inert propellants, dichiorodifluoromethane, or dichlorotetrafluoroethane.

The carrier in the composition preferably comprises propylene glycol, emulsifying wax, polyoxyethylene-10-stearyl ether, ethoxylated cetyl and stearyl alcohols, stearath-10, cetyl alcohol, methyl paraben, propyl paraben, trolamine, purified water, cetyl alcohol, ethoxylated stearyl alcohol, dry ethanolamine, de-ionized water, a suitable propellent, or a mixture thereof.

Where the composition is in the foam of a suppository, the composition preferably comprises theobroma oil, glycerinated gelatin, hydrogenated vegetable oil, polyalkyl glycol, fatty acid ester of polyalkylene glycol, coconut oil base, hydrogenated fatty acid, monoglyceride, cocoa butter, petroleum oil, beeswax, glycerine, polyethylene glycol 600 dilaurate, hydrogenated cocoa glyceride, polyethylene glycol, or a mixture thereof.

Where the composition comprises a time-release substance, the time-release substance can comprise one or more of an acrylic-based resin coating, a methacrylic acid copolymer, an acrylic-based resin mixed with a suitable non-medicinal carrier selected from the group consisting of lactose, magnesium stearate, polyethylene glycol, polyvinyl pyrolidone, or sodium starch glycolate, cellulose or ethyl cellulose, a matrix composition comprised of a hydrophilic polymer and an enteric polymer, a cellulose derivative, polyvinyl acetate phthalate, or polyvinyl acetate phthalate mixed with a plasticizer, a polysaccharide which is decomposable in the bowel, a locust bean gum or a guar gum, a film-forming polymer having hydrophilic groups, a film-forming acrylic polymer in admixture with a polysaccharide comprising from 30 to 100% by weight of at least one monomer selected from the group consisting of lower alkyl esters of acrylic acid and lower alkyl esters of methacrylic acid, a hydrocolloid gum obtained from a higher plant, or an anionic carboxylic polymer that does not dissolve at a pH below about 4, but is soluble at a pH ranging from about 4 to about 7.5.

The composition can be provided as a coated polymer. For example, in one embodiment, the composition comprises between about 0.1% by weight to about 90% by weight of an inosine compound coated with about 5% by weight to about 29% by weight of a hydrophilic polymer, and from about 0.5% by weight to about 25% by weight of an acrylic polymer that dissolves at a pH in the range of about 5.0 to about 7.5.

In some embodiments, the compositions are capsules or a tablets.

In some embodiments, the inosine compounds are enterically coated so as to be releasable in the terminal portion of the ileum and in the colon.

In some embodiments, the inosine compounds are present in unit dosage form adaptable for oral administration. Preferably, the unit dosage form is effective to relieve a symptom of an inflammation disease or a reperfusion disease without dose-limiting systemic toxicity.

Also provided by the invention is an enema formulation for treating or preventing a condition associated with an inflammatory bowel disease. The formulation includes the inosine compound in an amount effective to relieve a symptom of the inflammatory bowel disease without dose-limiting systemic toxicity.

In some embodiments, the formulation is provided in combination with a flowable carrier, which amount is released in the lower intestinal tract. The flowable carrier can be, e.g., water, alcohol, or an aqueous alcohol mixture. If desired, the flowable carrier can be thickened with one or more of gums, acrylates, or modified celluloses.

The formulation may additionally include a lubricant or a foaming agent. The formulation in some embodiments if provided in a form suitable for delivery from a prefilled bag or syringe. If desired, the enema formulation can be provided in a form suitable for delivery from a pressurized container.

The invention includes compositions comprising one or more inosine compounds described herein. Pharmaceutical composition may include those suitable for oral, rectal, nasal, topical (including buccal and sub-lingual), vaginal or parenteral (including intramuscular, sub-cutaneous and intravenous) administration, or for administration by inhalation or insufflation. The formulations may, where appropriate, be conveniently presented in discrete dosage units and may be prepared by any of the methods well known in the art of pharmacy. All such pharmacy methods include the steps of bringing into association the inosine compound with liquid carriers or finely divided solid carriers or both as needed and then, if necessary, shaping the product into the desired formulation.

Pharmaceutical formulations suitable for oral administration may conveniently be presented: as discrete units, such as capsules, cachets or tablets, each containing a predetermined amount of the active ingredient; as a powder or granules; or as a solution, a suspension, or as an emulsion. The inosine compounds may also be presented as a bolus electuary or paste, and be in a pure form, i.e., without a carrier. Tablets and capsules for oral administration may contain conventional excipients such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. The tablets may optionally be formulated so as to provide slow or controlled release of the inosine compound therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for enteral or rectal administration may be presented as a suppository with the usual carriers such as cocoa butter or polyethylene glycol. Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia. For intra-nasal administration the inosine compounds may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

The inosine compounds can also be administered to a patient in the form of a topical drug formulation. The topical drug formulation comprises an effective amount of an inosine compound. Examples of pharmaceutically acceptable carriers useful in a topical formulation include ointments, gel, emulsions, creams, lotions. Such formulations may further comprise oils, water, waxes and surfactants. The topical drug formulation can be administered via a transdermal patch. The transdermal patch can comprise an inosine compound and a backing layer.

For administration by inhalation, the inosine compounds are conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the inosine compounds may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

When desired, the above-described formulations, adapted to give sustained release of the active ingredient, may be employed. The pharmaceutical compositions may also contain other active ingredients such as antimicrobial agents, immunosuppressants, or preservatives.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited below, or an appropriate fraction thereof, of the active ingredient.

For each of the aforementioned conditions, the inosine compounds may be administered at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The pharmaceutical composition preferably is administered orally or enterally, and the precise amount administered to a patient will be the responsibility of the attendant physician. However, the dose employed will depend upon a number of factors, including the age and sex of the patient, the precise disorder being treated, and its severity. Also the route of administration may vary depending upon the condition and its severity.

When administered to a patient, the inosine compounds are preferably administered in isolated form. As used herein, "isolated" means that the inosine compounds are separated from other components of either (a) a natural source, such as a plant or cell, or (b) a synthetic organic chemical reaction mixture. Preferably, via conventional techniques, the inosine compounds are purified. As used herein, "purified" means that when isolated, the isolate contains at least 95%, preferably at least 98%, of a single inosine compound by weight of the isolate.

When an inosine compound contains one or more $SO_3^-$, $PO_3^{2-}$, $P_2O_3^{3-}$ or $P_3O_9^{4-}$ groups, it will be understood that the inosine compound is associated with one or more cations. Illustrative examples of cations useful in the invention are $Na^+$, $Li^+$, $K^+$, $Rb^+$, $Cs^+$, $Be^{2+}$, $Mg^{2+}$, $Ca^{2+}$, $Sr^{2+}$, $Ba^{2+}$, $Al^{3+}$, $Fe^{3+}$, $Cu^{2+}$, $Zn^{2+}$, $NH_4^+$; and alkyl or acyl ammonium salts such as $RNH_3^+$, $(R)_2NH_2^+$, $(R)_3NH^+$, where each R is independently an alkyl or aryl group.

The inosine compound can also be a zwitterion. In this regard, the inosine compound can contain one or more $SO_3^-$, $PO_3^{2-}$, $P_2O_3^{3-}$ or $P_3O_9^{4-}$ groups, and one or more of the inosine compound's nitrogen atoms can be protonated.

6. EXAMPLES

Example 1

Inosine Inhibits In Vitro Macrophage Release of IL-12 and TNF

To determine the effect of inosine on inflammatory cytokine production, stimulated macrophages were exposed to inosine at 0 to 1000 $\mu$M, after which production of cytokines IL-12 and TNF was measured. The results are shown in Table 1. Inosine was found to inhibit the release of these cytokines. These results demonstrate that inosine is useful for treating or preventing an inflammation disease or a reperfusion disease.

TABLE 1

EFFECT OF INOSINE ON IL-12 AND TNF PRODUCTION BY
PERITONEAL MACROPHAGES STIMULATED WITH LPS/IFN-γ

| Inosine (μM) | IL-12 (ng/ml) | TNF (ng/ml) |
|---|---|---|
| 0 (control) | 6.84 ± 0.39 | 16.81 ± 1.89 |
| 10 | 5.9 ± 0.19 | 10.08 ± 1.3 |
| 30 | 5.1 ± 0.14 | 8.38 ± 0.14 |
| 100 | 4.46 ± 0.62 | 7.61 ± 0.33 |
| 300 | 4.94 ± 0.06 | 5.45 ± 0.52 |
| 1000 | 4.34 ± 0.39 | 5.62 ± 0.88 |

Example 2

Inosine Inhibits Inflammatory Cytokine Responses
In Vivo While Increasing Anti-inflammatory
Cytokine Release To determine whether inosine inhibits inflammatory cytokine release in vivo, male BALB/c mice were injected with inosine (100 mg/kg; i.p.) followed 30 minutes later by an i.p. injection of LPS (70 mg/kg). Plasma levels of the different cytokines were measured at various times (90 mm 2 h, 4 h, and 8 h) after the LPS challenge.

Figure 1:
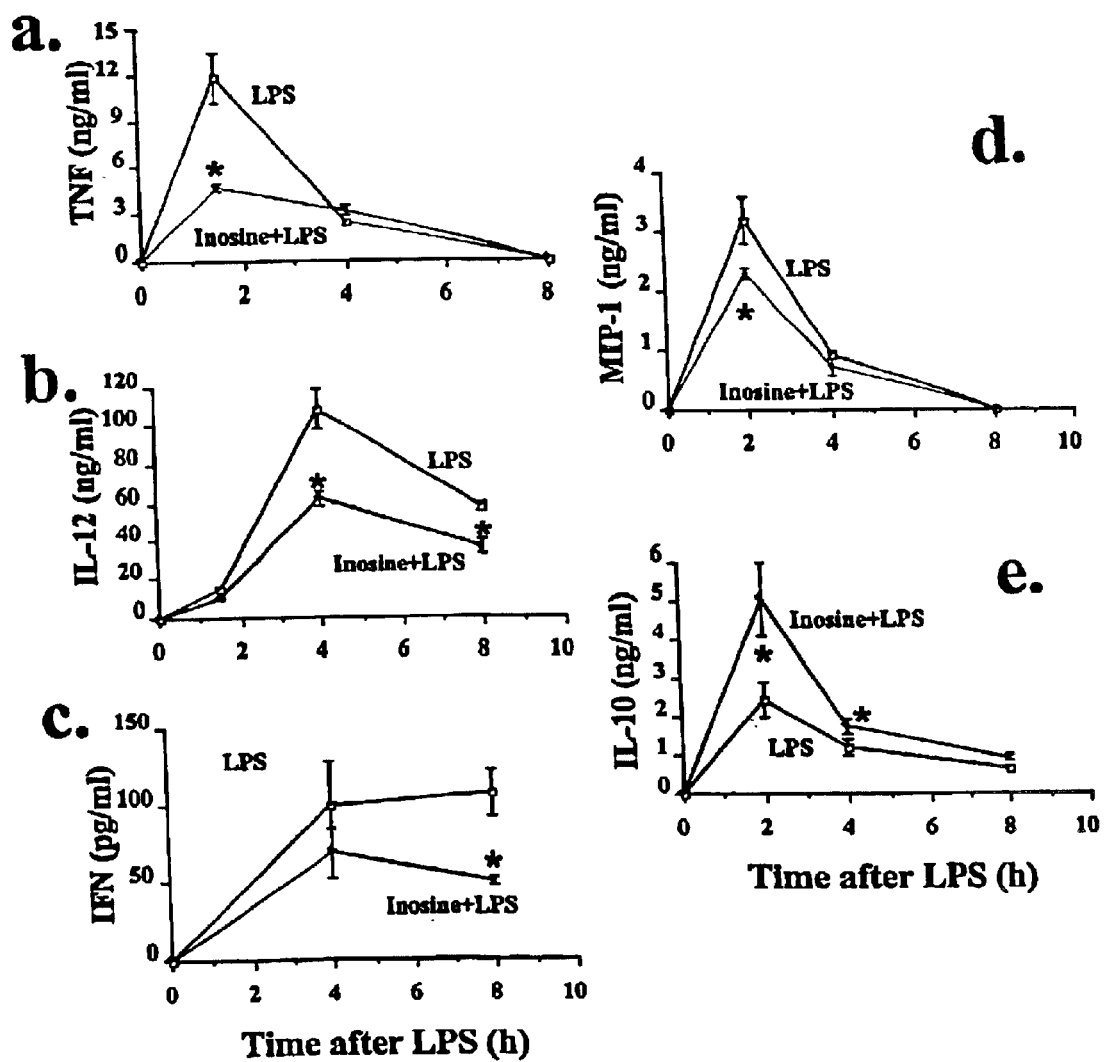
FIG. 1 is a schematic drawing showing the release of various cytokines over time following administration of LPS or LPS+inosine to mice.

The results are shown in FIGS. 1A–E. Data are mean ±SEM of n=8 mice. The asterisk in the figure indicates p<0.05. Inosine was observed to suppress the production of TNF-α (FIG. 1A), IL-12 (FIG. 1B), IFN-γ (FIG. 1C), and MIP-1α (FIG. 1D). Inosine was also shown to augment IL-10 (FIG. 1E) production in endotoxemic mice. These results were similar to the effect of inosine on cytokine release by macrophages in vitro. Notably, inosine suppressed the production of IFN-γ, which is involved in the proinflammatory effects of LPS. Taken together, these data demonstrate that inosine selectively and differentially alter the production of cytokines in vivo. Inosine inhibits the production of proinflammatory cytokines, but also potentiates the formation of the anti-inflammatory IL-10. Accordingly, inosine is useful for treating or preventing an inflammation disease or a reperfusion disease.

Example 3

Inosine Protects Against Lethal Challenge of LPS
in an In Vivo Model System

Figure 2:
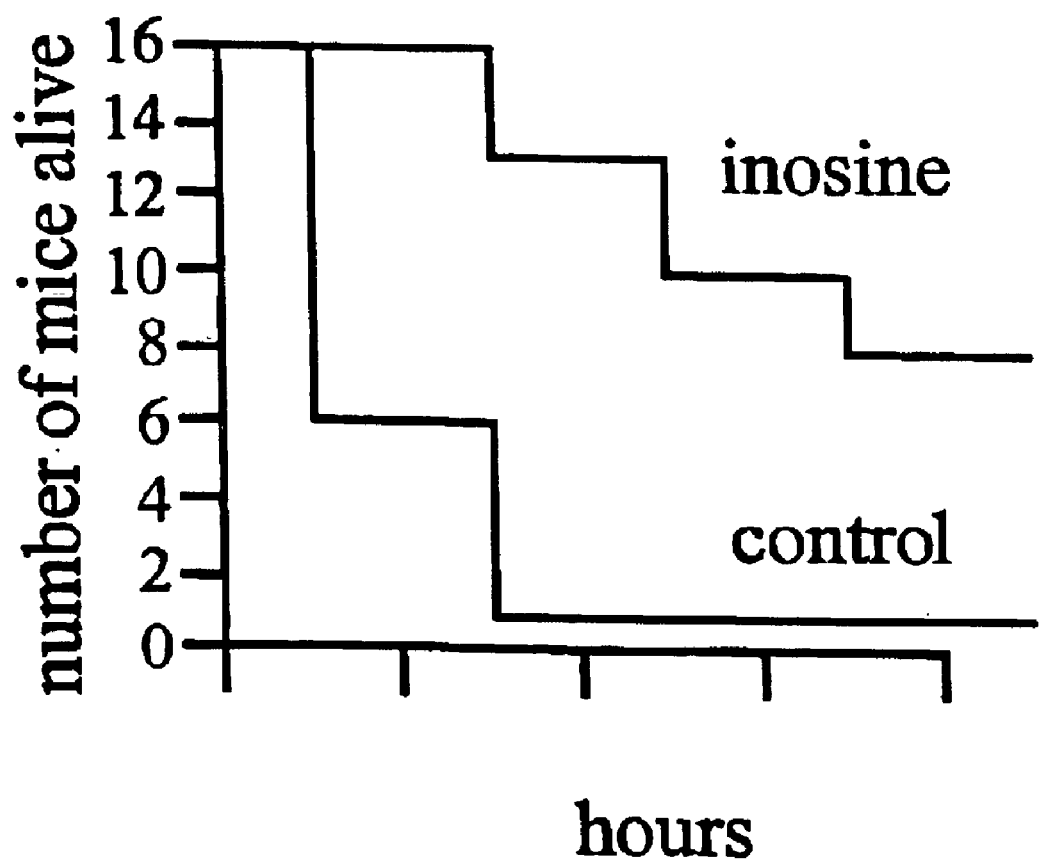
FIG. 2 is a graph showing the number of mice surviving (y-axis) over time (x-axis) following exposure to challenge with LPS following pretreatment with drug vehicle (physiologic saline) or 100-mg/kg inosine.
Figure 3:
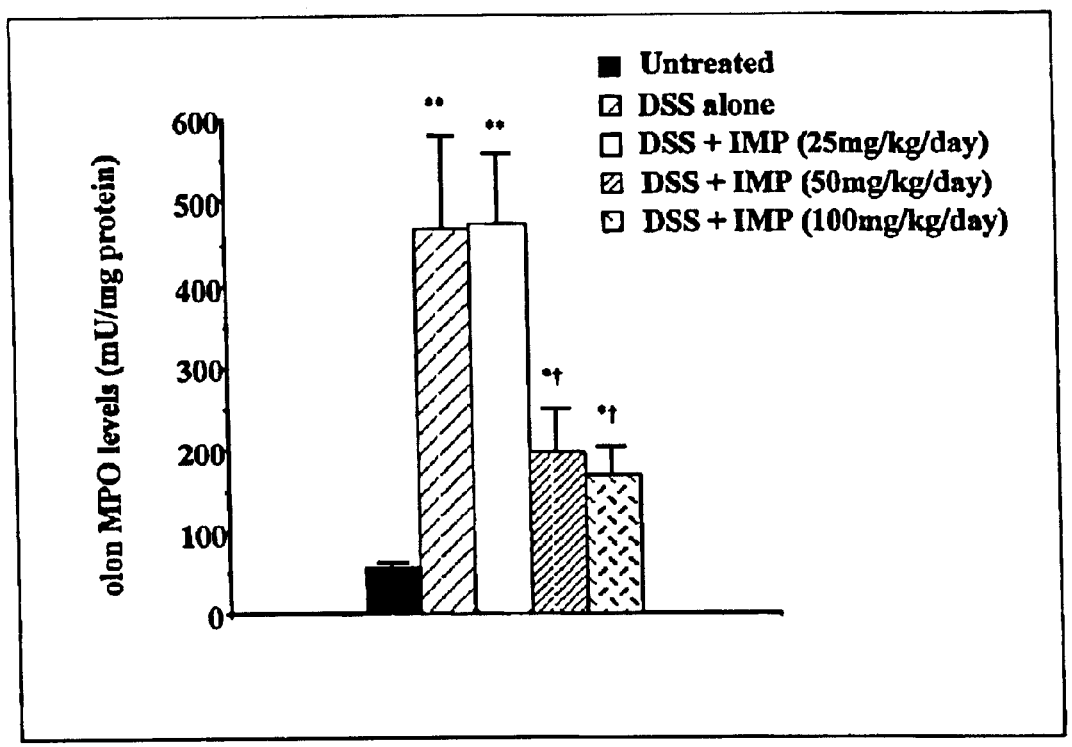
FIG. 3 is a graph showing the effect of various concentrations of inosine monophosphate (5'-IMP) on levels of MPO and MDA in the colon of mice with acute colon inflammation induced by DSS.

Because inosine skewed the cytokine response towards an anti-inflammatory profile, the ability of inosine to decrease LPS-induced lethality in a murine model system was investigated. BALB/c mice were pretreated with drug vehicle (physiologic saline) or 100 mg/kg inosine 30 min before the injection of 70 mg/kg of i.p. LPS. The results are shown in FIG. 2. Survival was recorded at 24, 48, 72, and 96 h after the LPS injection. Results from the summary of two different experiments are shown. N=16 animals in each group. Inosine improved survival rate at 24–96 h (p<0.05). Therefore, inosine conferred significant protection in this endotoxemic model. Thus, inosine is useful for treating or preventing an inflammation disease or a reperfusion disease.

Example 4

Inosine Inhibits the Development of Diabetes-
associated Symptoms in an In Vivo Model System Autoimmune diabetes is associated with a strong inflammatory component, along with activation of macrophages and infiltration of mononuclear cells into the pancreas. The subsequent inflammatory processes bring about the deleterious consequences of inflammation diabetes, such as islet inflammation, islet cell destruction, insulin deficiency, and hyperglycemia (Rabinovitch et al., Biochem. Pharmacol. 15:1139–49, 1998; Almawi et al., J. Clin. Endocrinol. Meatab. 84:1497–502, 1999). Cytokines produced mainly by macrophages have been reported to be central mediators in the intraislet inflammatory processes.

The effect of inosine was in a rat model of streptozotocin-induced diabetes was examined. Mice were treated with streptozotocin (40 mg/kg in citrate buffer) or vehicle (citrate buffer) i.p. for 5 consecutive days to induce diabetes. Blood glucose was monitored over the following 21 days using a one-touch blood glucose meter (Lifescan). Blood glucose was measured on days 1, 7, and 21 from blood obtained from the tail vein. Hyperglycemia was defined as non-fasting blood glucose level higher than 200 mg/dL. Mice were treated simultaneously with streptozotocin injection throughout the 21 days of the experiments and with vehicle or inosine (100 mg/kg oral gavage, twice a day). Samples of pancreas were removed on day 21 and weighed before being placed into 6 mls of acid ethanol (23:7:0.45 ethanol:dH$_2$O:HCl) and homogenized. The pancreas samples were incubated for 72 h at 4° C. before being centrifuged. The insulin content of the supernatant was then determined using an ELISA assay.

TABLE 2 shows mean and median glucose levels, and incidence of diabetes in streptozotocin (STZ) diabetic mice receiving vehicle or inosine treatment. An "*" indicates significant reduction of circulating glucose or diabetes incidence in the inosine-treated streptozotocin rats when compared to vehicle-treated streptozotocin rats (p<0.05).

TABLE 2

CHANGE IN GLUCOSE LEVELS IN STZ DIABETIC MICE
RECEIVING VEHICLE OR INOSINE

| | Mean Blood Glucose (mg/dl) | | | Median Blood Glucose (mg/dl) | | | Diabetes Incidence (%) | | |
|---|---|---|---|---|---|---|---|---|---|
| Days | 0 | 7 | 21 | 0 | 7 | 21 | 0 | 7 | 21 |
| Control | 96 ± 4 | 103 ± 3 | 91 ± 5 | 95 | 100 | 93 | 0 | 0 | 0 |
| STZ (vehicle) | 93 ± 3 | 137 ± 7 | 231 ± 15 | 94 | 146 | 260 | 0 | 8 | 67 |

TABLE 2-continued

CHANGE IN GLUCOSE LEVELS IN STZ DIABETIC MICE
RECEIVING VEHICLE OR INOSINE

| | Mean Blood Glucose (mg/dl) | | | Median Blood Glucose (mg/dl) | | | Diabetes Incidence (%) | | |
|---|---|---|---|---|---|---|---|---|---|
| Days | 0 | 7 | 21 | 0 | 7 | 21 | 0 | 7 | 21 |
| STZ (inosine) | 95 ± 4 | 112 ± 6* | 152 ± 20* | 96 | 117* | 130* | 0 | 0 | 25* |

The relative effect of vehicle and inosine on pancreatic insulin content in STZ diabetic mice is shown in TABLE 7. An "*" in TABLE 7 indicates significant decreases in insulin content in response to streptozotocin when compared to control, and a "#" indicates significant preservation of pancreatic insulin content in the inosine-treated streptozotocin rats ($p<0.05$). Pancreatic insulin content at 21 days in streptozotocin diabetic mice receiving vehicle or inosine treatment.

TABLE 3

PANCREATIC INSULIN CONTENT AT 21 DAYS IN STZ
DIABETIC MICE RECEIVING VEHICLE OR INOSINE

| | Pancreatic insulin content (ng insulin/mg protein) |
|---|---|
| Control | 68 ± 11 |
| Streptozotocin (Vehicle treated) | 6 ± 1* |
| Streptozotocin (Inosine treated) | 21 ± 4# |

Vehicle-treated animals developed diabetes, as demonstrated by progressive hyperglycemia (Table 2) and the suppression of pancreatic insulin content (Table 3). In contrast, animals treated with inosine showed significant reductions in the incidence of diabetes, and mean and median plasma glucose levels. They also showed a significant preservation of pancreatic insulin content (Table 3). These data indicate that inosine is useful for treating or preventing diabetes.

Example 5
Inosine Inhibits the Development of Inflammatory Bowel Disease Symptoms in an In Vivo Model System The effect of inosine in a mouse model of inflammatory disease was examined. Inosine was administered (oral administration, 100 mg/kg, 2 times a day), in a mouse model of inflammatory bowel disease induced by dextran sulfate solution (DSS). This system is well-characterized and is considered a reliable model of inflammatory bowel disease. Efficacy of a pharmaceutical compound in this model is taken as evidence that the compound is likely to be effective in human beings (Sasaki et al., Scand. J. Immunol. 51:23–8, 2000; Gaudio et al, Dig. Dis. Sci. 44:1458–75, 1999; Murthy et al., Aliment Pharmacol. Ther. 13:251–60, 1999; Kimura et al., Arzneimittelforschung 48:1091–96, 1998; Dieleman et al., Scand. J Gastroenterol. Suppl. 223:99–104, 1997).

Symptoms associated with the DSS model were induced as follows. Mice were patiented to a drinking water containing 5% DSS for 10 days, in the presence (n=10) or absence (n=10) of inosine treatment (200 mg/kg/day, orally). At the end of 10 days, animals were evaluated for the incidence of bloody diarrhea, for colon shortening, and colon histopathology. Colonic myeloperoxidase (MPO) and malondialdehyde (MDA) levels were measured. These parameters provide a good cross-section of the functional and inflammatory changes associated with the current model of inflammatory bowel disease.

The results are shown in Table 4. The data demonstrate the protective effect of inosine on functional and inflammatory parameters of colitis. Significant protective effect of inosine in the presence of DSS is indicated as *$p<0.05$, when compared to the values with DSS alone in the absence of inosine.

TABLE 4

EFFECT OF INOSINE ON PARAMETERS ASSOCIATED
WITH COLITIS IN DSS MICE

| Functional or inflammatory parameter | Control (no DSS) | IBD (DSS) | IBD (DSS) with inosine |
|---|---|---|---|
| Weight loss of the animals at 10 days (%) | −7 ± 3 | 20 ± 2 | 13 ± 1* |
| Colonic length | 6.0 ± 0.2 | 4.2 ± 0.1 | 5.1 ± 0.1* |
| Incidence of rectal bleeding (%) | 0 | 90 | 20* |
| Gut histological damage (1–4 scale) | 0 | 3.6 ± 0.4 | 1.2 ± 0.4* |
| Gut myeloperoxidase levels (nU/mg protein) | 52 ± 9 | 296 ± 87 | 88 ± 14* |
| Gut malondialdehyde levels (nmol/mg protein) | 1.9 ± 0.2 | 3.7 ± 0.8 | 2.1 ± 0.5* |

Inosine treated mice responded to DSS with an improved colonic function, reduced colon shortening, and reduction in the inflammatory response in the gut. Thus, inosine is useful for treating or preventing an inflammation disease, more particularly, an inflammatory bowel disease, even more particularly, colitis.

Example 6

Inosine Adducts Modulate Inflammatory Bowel Disease Symptoms in an In Vivo Model System The effect of inosine 5'-monophosphate (5'-IMP) on levels of myeloperoxidase (MPO) and malondialdehyde (MDA) in the colon of mice with DSS-induced acute colon inflammation was examined. Mice were exposed to DSS ad libitum for 10 days. Treatment with 5'-IMP (25, 50, or 100 mg/kg/day, BID) then commenced on day 1. On day 10 the colon was removed and biopsies were taken for determination of MDA and MPO levels.

The results are shown in FIG. 2. The data are expressed as mean ±SEM from 10 animals, statistical analysis was conducted using Student's unpaired t-test where $p<0.05$ was considered significant. An asterisk (*) indicates $p<0.05$, a double asterisk (**) indicates $p<0.01$ relative to untreated animals, and a dagger (†) indicates $p<0.01$ relative to DSS treated animals. 5'-IMP administered at dosages of 50 mg/kg/day or 100 mg/kg/day significantly lowered levels of MPO in mice.

The effect of 5'-IMP on the survival of mice with acute colon inflammation induced by DSS was also examined. Mice were exposed to DSS ad libitum for 20 days, after which treatment with inosine monophosphate (50 or 100 mg/kg/day, BID) commenced on day 1. The number of mice surviving each day was recorded. The data are expressed as % survival from 10 animals, statistical analysis was conducted using $\chi^2$ where $p<0.05$ was considered significant.

Figure 4:
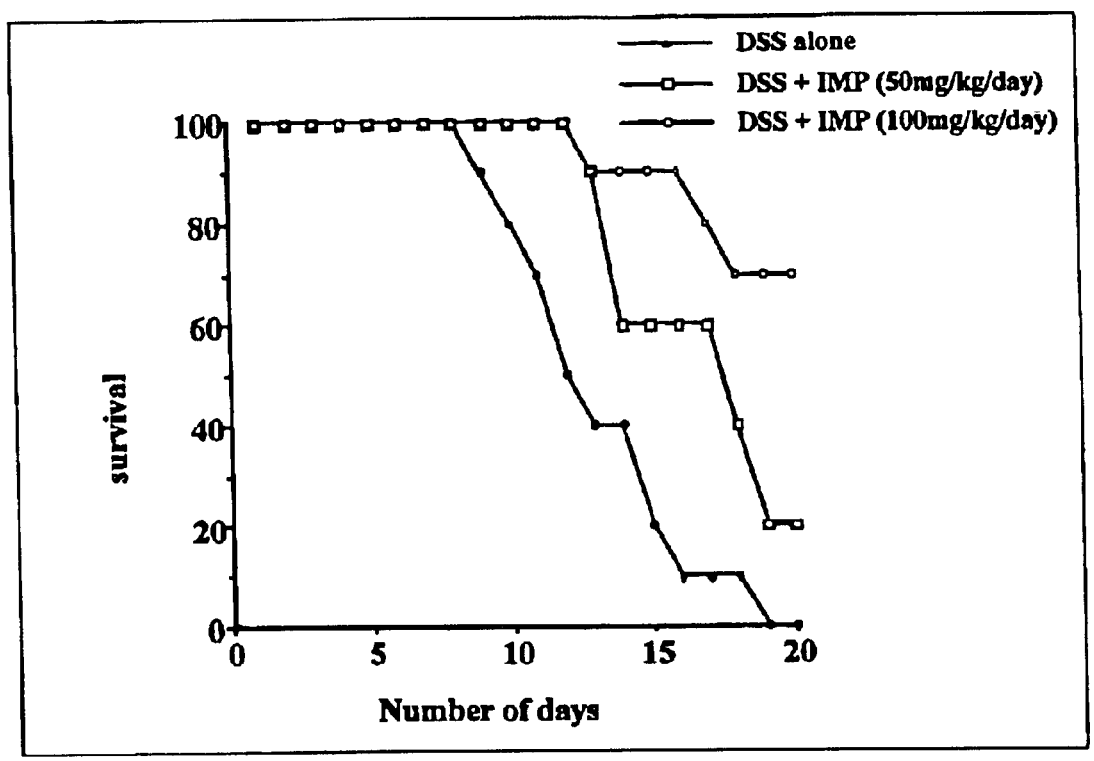
FIG. 4 is a graph showing the effect of inosine monophosphate on the survival of mice with acute colon inflammation.
Figure 5:
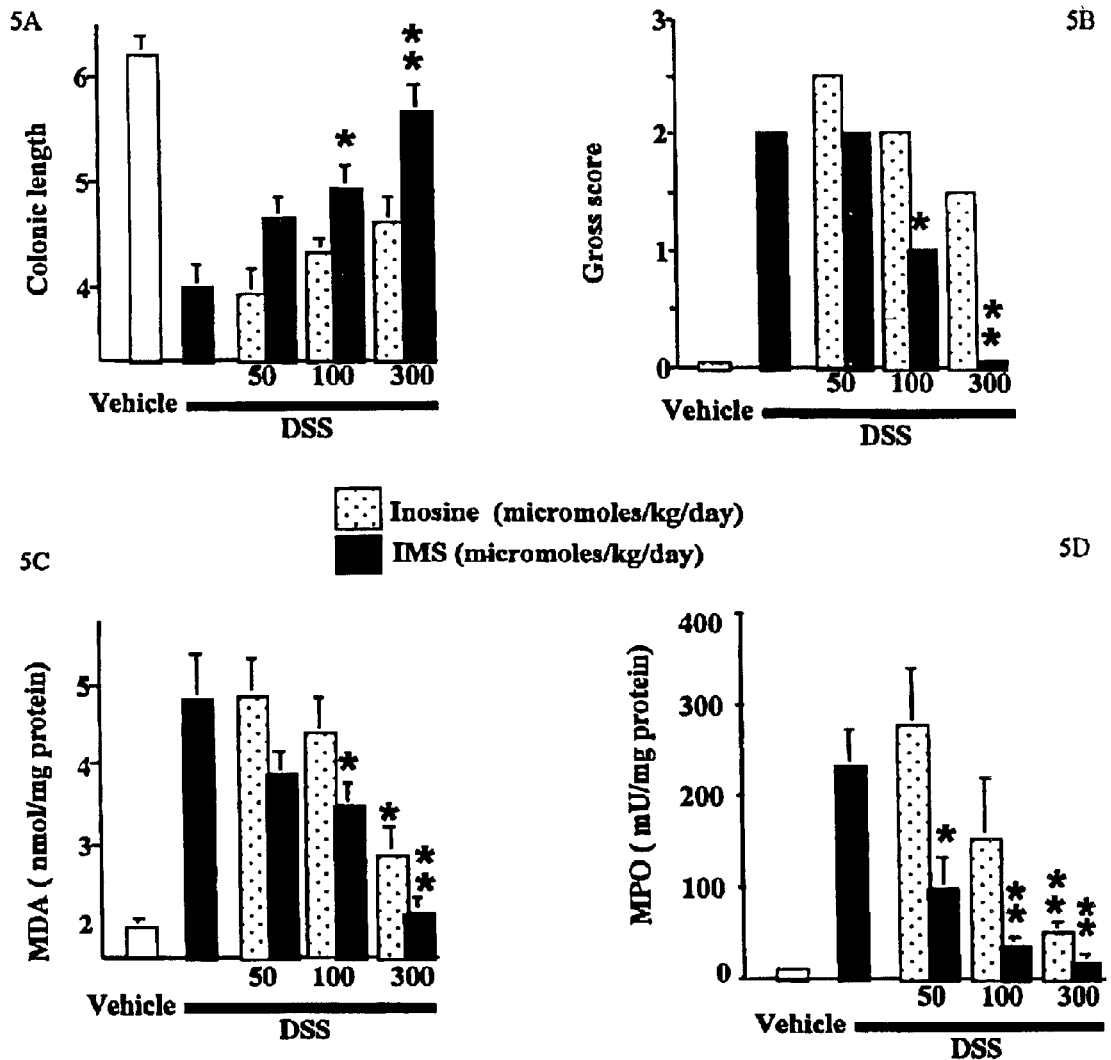
FIGS. 5A–5D are graphs showing the effect of various doses (50, 100 and 300 μmoles/kg/day) of inosine and inosine 5'-monosulfate (5'-IMS) on dextram sodium sulfate-induced colitis in mice.

The results are shown in FIG. 4. Addition of 5'-IMP at either dose significantly increased the number of surviving mice at days 10–20 relative to the number of surviving mice not treated with 5'-IMP.

The protective effect of 5'-IMP on body weight, colon length, rectal bleeding, and colon histopathology was also examined. Male Balb/c mice were initially weighed and body weights recorded before being exposed to the DSS solution (5% w/v) ad libitum in their drinking water. Inosine monophosphate (5'-IMP) at various concentrations was administered orally BID starting on day 1. On day 10 the experiment was terminated and the animals were re-weighed and sacrificed. The colon was dissected out and measured, animals were also assessed for obvious rectal bleeding and the colon scored for gross histological changes (0=normal colon, 1=colon with small amount of blood present mixed with feces, 2=colon with large amount of blood present with feces, 3=colon filled with blood no feces). Samples were taken and analyzed for biochemical changes and for sectioning.

The results are shown in Table 5. The data are expressed as mean ±SEM, n=10. Statistical analysis was conducted using Student's unpaired t-test or Fisher's exact test where $p<0.05$ was considered significant. (*) indicates $p<0.01$ vs. untreated animals, and a (†) indicates $p<0.01$ vs. DSS treated animals.

TABLE 9

EFFECT OF 5'-IMP ON PARAMETERS ASSOCIATED WITH COLITIS IN DSS MICE

| Groups | % decrease in body weight | Colon Length (cm) | Rectal Bleeding | Gross Histological score (median) |
|---|---|---|---|---|
| Untreated | −7.2 ± 3.5 | 6 ± 0.2 | 0/10 | 0 |
| DSS treated | 22.8 ± 1.8* | 3.5 ± 0.2* | 8/10* | 3 |
| DSS + Inosine 5'-monophosphate (25 mg/kg/day) | 18.3 ± 1* | 4.5 ± 0.3*† | 3/10*† | 1 |
| DSS + Inosine 5'-monophosphate (50 mg/kg/day) | 16.8 ± 1*† | 4.7 ± 0.3*† | 3/10*† | 0 |
| DSS + Inosine 5'-monophosphate (100 mg/kg/day) | 16.4 ± 1.2*† | 4.9 ± 0.2*† | 0/10† | 0 |

Treatment with 5'-IMP mitigated the effects of DSS-associated colitis in all properties examined. In particular, 5'-IMP inhibited the weight loss and decrease in colon length observed in DSS-treated mice. Fewer 5'-IMP-treated mice exhibited rectal bleeding, and the gross histological scores of 5'-IMP-treated mice were either identical to untreated mice (50 mg/kg/day or 100 mg/kg/day 5'-IMP) or showed minor histopathological alterations relative to untreated mice (25 mg/kg/day).

The effect of various doses (50, 100 and 300 μmoles/kg/day) inosine and IMS on the outcome of DSS (dextran sodium sulfate) colitis in mice. Colonic length, gross histologic score, colonic MDA content and colonic MPO content have been determined. N=10 animals per experimental groups. *$p<0.05$ and **$p<0.01$ indicates significant improvements in drug treated DSS animals, when compared to vehicle treated DSS animals. Mean +SEM are presented, except for histological scores, which are presented as medians.

The results are shown in FIGS. 5A–5D. Significant improvements in 5'-IMS treated DSS animals was observed as compared to vehicle treated DSS animals. Mean ±SEM are shown, except for the histological scores, which are presented as medians. In these studies, 5'-IMS, but not inosine, provided significant protection against colonic shortening and visible histological damage. Furthermore, 5'-IMS provided significant protection against the DSS induced increases in colonic malondialdehyde (MDA; a marker of lipid peroxidation) and myeloperoxidase (MPO; a measure of neutrophil infiltration) content at a lower dose level, relative to inosine. For example, 5'-IMS substantially reduced MDA levels at 50 μmoles/kg/day, whereas inosine reduced MDA levels only at 100 μmoles/kg/day. Similarly, 5'-IMS substantially reduced MDA levels at 50 μmoles/kg/day, whereas inosine reduced MDA levels at only at 300 μmoles/kg/day.

Accordingly, inosine 5'-monophosphate and inosine 5'-nonsulfate are useful for treating or preventing an inflammation disease, in particular, an inflammatory bowel disease, more particular, colitis.

Example 7

Inosine 5'-monosulfate Substantially Reduces the Severity and the Incidence of Collagen-induced Arthritis in Mice The effect of 5'-IMS in a murine model system of collagen-induced arthritis was studied. Male DBA/1J mice were injected intradermally on day 1 with 0.1 mL of an emulsion of bovine type II collagen plus complete Freunds's adjuvant (CFA). A second injection was administered on day 21. Treatment with 5'-IMS (100 or 200 mg/kg/day, BID) per gavage was begun on the day of the second collagen/CFA injection and continued throughout the study, which was terminated on day 45 (24 days after the second injection).

Mice were evaluated daily for arthritis by using a macroscopic scoring system ranging from 0–4 (0=no signs of arthritis, 1=swelling or redness of the paw or one digit, 2=two joints involved, 3=more than 2 joints involved, 4=severe arthritis of the entire paw). The arthritic index for each mouse was calculated by adding the four scores of the individual paws. Severity indices were calculated for the whole groups of mice (vehicle- or 5'-IMS-treated), with no animal being excluded from the calculations, as well as the percentage of the treatment group exhibiting signs of arthritis. At study termination, paws were removed from all animals in each treatment group and randomly assigned to MPO, MDA or chemokines/cytokine measurements.

Arthritis was induced in DBA/1J mice by two 100 μL sub-dermal injections of a 1:1 mixture of bovine collagen type II (1 mg/mL) and complete Freund's adjuvant (1 mg/mL) 21 days apart. Gavage treatment with 5'-IMS (100 or 200 mg/kg/day, BID) commenced on the day of the second injection. Both 5'-IMS dosing regimens significantly reduced the prevalence of arthritis from 90% to 25% on day 24 post second collagen injection. 5'-IMS also significantly reduced the severity of arthritis. Statistical analysis was performed by Student's t-test or fisher's exact test as appropriate. The results (FIGS. 6A–B) demonstrated that 5'-IMS substantially reduced the severity and the incidence of disease. Accordingly, 5'-IMS, an illustrative inosine compound, is useful for treating or preventing arthritis in a patient.

Example 8

Inosine 5'-monosulfate Dose-dependently Reduces the Severity and the Incidence of Chemokine and Pro-inflammatory Cytokine Expression in Joints The effect of 5'-IMS on the levels of the chemokine MIP-1α and the cytokines 1L-12 and TNF-α in paws of DBA/1J mice treated with subdermal injections of collagen to induce arthritis was studied. Gavage treatment with 5'-IMS (100 or 200 mg/kg/day, BID) commenced on the day of the second collagen injection and paws were taken 24 days later and homogenized for analysis. 5'-IMS at a dose of 200 mg/kg/day significantly reduced the levels of MIP-1α and TNF-α, and tended to reduce IL-12 levels (p=0.09). Data are expressed as mean ±SEM from n=10 animals. Statistical analysis was conducted using Student's unpaired t-test where p<0.05 was considered significant; p<0.05 vs. untreated mice. The results (FIG. 7) demonstrate that 5'-IMS dose-dependently reduced the severity and the incidence of chemokine and pro-inflammatory cytokine expression in joints. Accordingly, 5'-IMS, an illustrative inosine compound, is useful for treating or preventing an inflammation disease, particularly arthritis, in a patient.

Example 9

Inosine 5'-monosulfate Profoundly Reduces Neutrophil Infiltration (Reflected by MPO Concentration) and Lipid Peroxidation (Reflected by MDA) in Joints The effect of 5'-IMS on the levels of MPO and MDA in paws of DBA/1J mice treated with subdermal injections of collagen to induce arthritis was studied. Gavage treatment with 5'-IMS (100 or 200 mg/kg/day, BID) commenced on the day of the second collagen injection and paws were taken 24 days later and homogenized for MPO and MDA measurements. Data are expressed as mean ±SEM from n=10 animals. Statistical analysis was conducted using Student's unpaired t-test where p<0.05 was considered significant. * p<0.05, **p<0.01 vs. control mice and †p<0.05 vs. untreated mice. The results (FIGS. 8A–B) demonstrate that 5'-IMS profoundly reduced neutrophil infiltration (reflected by MPO concentration) and lipid peroxidation (reflected by MDA) in joints. Accordingly, 5'-IMS, an illustrative inosine compound, is useful for treating or preventing an inflammation disease, particularly arthritis, in a patient.

Example 10

Synthesis of Inosine 5' Monosulfate (5'-IMS), Sodium Salt

Method A:

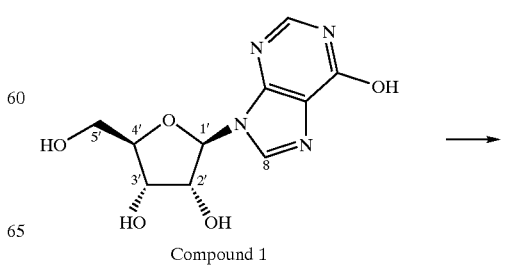

Compound 1

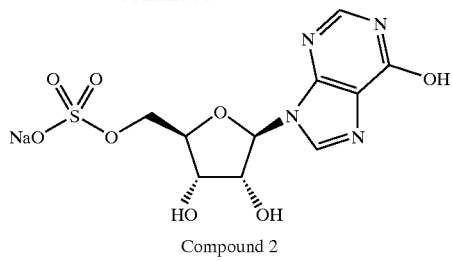

Compound 2

Inosine (Compound 1) (5.00 g, 18.7 mmol) was dried overnight by dean-stark distillation in 100 mL anhydrous benzene. The benzene was removed under high vacuum for 1 day, and 100 mL anhydrous dimethylformamide added by syringe under nitrogen atmosphere. An addition funnel was attached, purged with nitrogen, and charged with 3.87 g (1.3 eq.) $SO_3$-pyridine complex in 52 mL anhydrous dimethylformamide. The inosine suspension was solvated by warming to 100° C., followed by rapid cooling to room temperature.

The $SO_3$-pyridine complex was added dropwise over a half hour with vigorous stirring, then stirred at room temperature under nitrogen for 4 hours. Sodium bicarbonate (2.04 g, 1.3 eq.) was added, followed by 2.0 mL deionized water. The resulting suspension was stirred until fully solubilized and gas evolution had ceased. Dimethylformamide and pyridine were removed under high vacuum for 2 days, and the crude material lyophilized to give 9.6 g of a fine white powder. This crude material was crystallized from 3:1 methanol:water, filtered, and the filtrate concentrated under vacuum to a light yellow oil. This was triturated overnight with 30 mL methanol, filtered, and the solids purified in eight 1.2 g volumes by flash chromatography on 120 g microcrystalline cellulose. A gradient was run starting with 500 mL of 90:5:5 acetonitrile: water:triflouroacetic acid, then 500 mL of 85:10:5 acetonitrile:water:triflouroacetic acid, then 500 mL of 80:15:5 acetonitrile:water:triflouroacetic acid, then 500 mL of 75:20:5 acetonitrile:water:triflouroacetic acid, and finally 500 mL of 75:25 acetonitrile:water. The combined fractions were reduced under vacuum, titrated to pH 7.5 with saturated aqueous sodium bicarbonate, and lyophilized to give 6.3 g (91%) of inosine 5'-monsulfate, sodium salt (compound 2), which is recovered as a fine white powder.

Method B:

2',3'-Isopropylidene Inosine 5'-monosulfate Pyridinium Salt.

2',3'-Isopropylidene inosine (50.00 g, 162.2 mmol) was dissolved with vigorous stirring in 350 mL anhydrous dimethylformamide. Sulfur trioxide-pyridine complex (38.72 g, 1.5 eq.) was dissolved in 100 mL anhydrous dimethylformamide with slight warming and stirring. The sulfur trioxide-pyridine solution was added via cannula into the vigorously stirred 2',3'-isopropylidene inosine solution. A white precipitate formed 0.5 h after the addition. The reaction was stirred overnight at room temperature under nitrogen atmosphere. The reaction mixture was then vacuum filtered, and the solids were twice suspended in 100 mL dimethylformamide and filtered. The solids were washed four times with 150 mL ethyl acetate, then dried in vacuo at 40 C overnight to yield 60.41 g (80% yield) of 2',3'-isopropylidene inosine 5'-monosulfate pyridinium salt as a fluffy white powder.

2',3'-Isopropylidene inosine 5'-monosulfate sodium salt. 2',3'-Isopropylidene inosine 5'-monosulfate pyridinium salt (60.30 g, 129.0 mmol) was suspended with vigorous stirring in 600 mL deionized water. The suspension was titrated to pH 7.0 with 5.0 N sodium hydroxide, during which time the solids dissolved. The solution was then lyophilized. The resulting white fluffy powder was dissolved in 200 mL deionized water by warming slightly, then titrated to pH 7.0 with 5.0 N sodium hydroxide. The solution was then lyophilized to give 52.07 g (98%) of 2',3'-isopropylidene inosine 5'-monosulfate sodium salt as a white fluffy powder.

Inosine 5'-monosulfate Sodium Salt

2',3'-Isopropylidene inosine 5'-monosulfate sodium salt (25.00 g, 60.92 mmol) was dissolved in 100 mL deionized water, and a stream of 400 mL trifluoroacetic acid was slowly added over 3 minutes to the stirred solution at room temperature. The resulting mixture was stirred for 15 min, and the concentrated to a viscous oil at 40° C. and at reduced pressure on a rotational evaporator. The resulting oil was consecutively dissolved four times in 150 mL deionized water, and it was concentrated to a viscous oil at 40° C. and at reduced pressure on a rotational evaporator. The oil was dried in vacuo overnight at room temperature. The resulting material was then crystallized from acetone/water to give a white powder. The powder was dissolved in 300 mL deionized water, vacuum filtered through a 0.45 micron nylon filter, and lyophilized to give 18.43 g (82%) of inosine 5'-monosulfate sodium salt as a white powder.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to call within the scope of the appended claims.

A number of references have been cited, the entire disclosures of which are incorporated herein by reference.

What is claimed is:

1. A method for treating an inflammatory bowel disease, comprising administering to a patient in need thereof an effective amount of a compound of formula I:

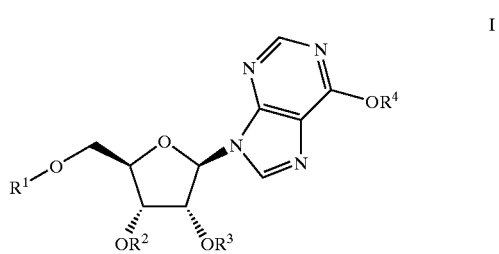

or a pharmaceutically acceptable salt thereof, wherein;
$R^1$ is $C_2$–$C_6$ acyl, $SO_3H$ or $P_2O_6H_3$; and
$R^2$, $R^3$ and $R^4$ are independently H, $C_2$–$C_6$ acyl, $SO_3H$, $PO_3H_2$, $P_2O_6H_3$ or $P_3O_9H_4$.

2. The method of claim 1, wherein $R^1$ is $C_2$–$C_6$ acyl, or $SO_3H$, or a pharmaceutically acceptable salt thereof.

3. The method of claim 1, wherein $R^1$ is $SO_3H$, or a pharmaceutically acceptable salt thereof.

4. The method of claim 1, wherein $R^1$ is $P_2O_6H_3$, or a pharmaceutically acceptable salt thereof.

5. The method of claim 1, wherein $R^1$ is $C_2$–$C_6$ acyl.

6. The method of claim 5, wherein the $C_2$–$C_6$ acyl is acetyl.

7. The method of claim 1, wherein the inflammatory bowel disease is ulcerative colitis or Crohn's disease.

8. A method for treating an inflammatory bowel disease, comprising administering to a patient in need thereof an effective amount of a compound of formula I:

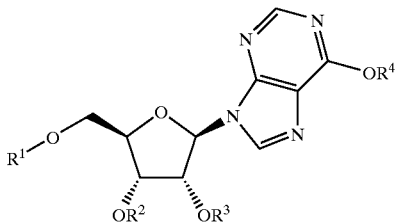

or a pharmaceutically acceptable salt thereof, wherein:

$R^1$ is $C_2$–$C_6$ acyl, $SO_3H$, $PO_3H_2$, $P_2O_6H_3$ or $P_3O_9H_4$; and $R^2$, $R^3$ and $R^4$ are independently H, $C_2$–$C_6$ acyl, $SO_3H$, $PO_3H_2$, $P_2O_6H_3$ or $P_3O_9H_4$.

9. The method of claim 8, wherein:

$R^1$ in $SO_3H$, or a pharmaceutically acceptable salt thereof; and $R^2$, $R^3$ and $R^4$ are H.

10. The method of claim 8, wherein:

$R^1$ is $PO_3H_2$, or a pharmaceutically acceptable salt thereof; and $R^2$, $R^3$ and $R^4$ are H.

11. The method of claim 8 wherein:

$R^1$ is $P_2O_6H_3$, or a pharmaceutically acceptable salt thereof; and $R^2$, $R^3$ and $R^4$ are H.

12. The method of claim 8 wherein:

$R^1$ is a $C_2$–$C_6$ acyl, and $R^2$, $R^3$ and $R^4$ are H.

13. A method for treating an inflammatory bowel disease, comprising orally or enterally administering to a patient in need thereof an effective amount of a compound of formula I:

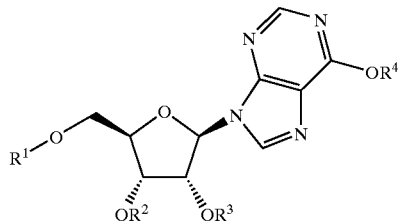

or a pharmaceutically acceptable salt thereof, wherein:

$R^1$, $R^2$, $R^3$ and $R^4$ are each independently H, $C_2$–$C_6$ acyl, $SO_3H$, $PO_3H_2$, $P_2O_6H_3$ or $P_3O_9H_4$.

14. The method of claim 13, where $R^1$, $R^2$, $R^3$ and $R^4$ are H.

15. The method of claim 13, where $R^1$ is $SO_3H$, or a pharmaceutically acceptable salt thereof, and $R^2$, $R^3$ and $R^4$ are H.

16. The method of claim 13 where $R^1$ is $PO_3H_2$, or a pharmaceutically acceptable salt thereof, and $R^2$, $R^3$ and $R^4$ are H.

17. The method of claim 13 where $R^1$ is $P_2O_6H_3$, or a pharmaceutically acceptable salt thereof, and $R^2$, $R^3$ and $R^4$ are H.

18. The method of claim 13 where $R^1$ is $P_3O_9H_4$, or a pharmaceutically acceptable salt thereof, and $R^2$, $R^3$ and $R^4$ are H.

19. The method of claim 13 where $R^1$ is $C_2$–$C_6$ acyl, and $R^2$, $R^3$ and $R^4$ are H.

20. The method of claim 1, wherein the $R^2$, $R^3$ and $R^4$ are —H; and $R_1$ is —$SO_3^-Na^+$.

21. The method of claim 8, wherein the $R^2$, $R^3$ and $R^4$ are —H; and $R_1$ is —$SO_3^-Na^+$.

22. The method of claim 13, wherein the $R^2$, $R^3$ and $R^4$ are —H; and $R_1$ is —$SO_3^-Na^+$.

23. The method of claim 8 wherein:

$R^1$ is $P_3O_9H_4$, or a pharmaceutically acceptable salt thereof; and $R^2$, $R^3$ and $R^4$ are H.

24. The method of claim 13, wherein the administering is orally administering.

25. The method of claim 13, wherein the administering is enterally administering.

26. The method of claim 8, wherein the inflammatory bowel disease is Crohn's disease.

27. The method of claim 8, wherein the inflammatory bowel disease is ulcerative colitis.

28. The method of claim 13, wherein the inflammatory bowel disease is Crohn's disease.

29. The method of claim 13, wherein the inflammatory bowel disease is ulcerative colitis.

* * * * *

UNITED STATES PATENT AND TRADEMARK OFFICE
CERTIFICATE OF CORRECTION

PATENT NO. : 6,958,324 B2
APPLICATION NO. : 10/107080
DATED : October 25, 2005
INVENTOR(S) : Andrew L. Salzman et al.

Page 1 of 1

It is certified that error appears in the above-identified patent and that said Letters Patent is hereby corrected as shown below:

Title page,
Item [54], Title, "INFLAMATION" should read -- INFLAMMATION --;
Item [74], Assignee, "Pickerinf" should read -- Pickering --;

Column 41,
Line 34, "in" should read -- is --;

Column 42,
Lines 32, 34 and 36, "$R_1$" should read -- $R^1$ --.

Signed and Sealed this

Twenty-seventh Day of June, 2006

JON W. DUDAS
*Director of the United States Patent and Trademark Office*